United States Patent
Spriggs et al.

(10) Patent No.: US 6,187,909 B1
(45) Date of Patent: Feb. 13, 2001

(54) VIRAL ENCODED SEMAPHORIN PROTEIN RECEPTOR POLYPEPTIDES

(75) Inventors: Melanie K. Spriggs; Michael R. Comeau, both of Seattle; Robert F. DuBose, Bellevue; Richard S. Johnson, Mercer Island, all of WA (US)

(73) Assignee: Immunex Corporation, Seattle, WA (US)

( * ) Notice: Under 35 U.S.C. 154(b), the term of this patent shall be extended for 0 days.

(21) Appl. No.: 09/459,066

(22) Filed: Dec. 10, 1999

Related U.S. Application Data

(62) Division of application No. 09/181,706, filed on Oct. 28, 1998, now Pat. No. 6,130,068, which is a continuation of application No. 08/958,598, filed on Oct. 28, 1997
(60) Provisional application No. 60/112,009, filed on Oct. 26, 1998.

(51) Int. Cl.$^7$ .......................... C07K 14/00; C07H 21/04; A61K 39/395
(52) U.S. Cl. ...................... 530/350; 530/300; 530/402; 435/69.1; 536/23.1; 424/192.1
(58) Field of Search .................. 530/350, 300, 530/402; 435/69.1, 7.1; 536/23.1; 424/192.1

(56) References Cited

FOREIGN PATENT DOCUMENTS

WO 93 16178  8/1993 (WO) .
WO 95 07706  3/1995 (WO) .

OTHER PUBLICATIONS

Adams, et al., "Human Brain Expressed Sequence Tag EST01773", *Geneseq Database entry Q61322, Accession Number Q61322*, Mar. 1994.

Chen, H., et al., "Neuropilin–2, a Novel Member of the Neuropilin Family is a High Affinity Receptor for the Semaphorins Sema E and Sema IV but not Sema III", *Neuron* 19: 547–559, 1997.

Comeau, et al., "A Poxvirus–Encoded Semaphorin Induces Cytokine Production from Monocytes and Binds to a Novel Cellular Semaphorin Receptor, VESPR", *Immunity* 8: 473–482, Apr. 1998.

Embl–est Database Accession No. N22685, yx65c01.s1 Homo sapiens cDNA clone 266496 3'. Submitted by Hillier et al., 1995.

Essner, A., et al., "Alcelaphine herpesvirus type 1 has a semaphorin–like gene", *Journal of General Virology* 76:1063–1067, 1995.

George et al., Current Methods in Sequence Comparison and Analysis, selected methods and applications. Edited by David H. Schlesinger, Alan R. Liss, Inc., New York, 124–129, 1988.

Hall, K.T., et al., "Human CD100, a novel leukocyte semaphorin that promotes B–cell aggregation and differentiation", *Proc. Natl. Acad. Sci. USA* 93:11780–11785, 1996.

He, Z., et al., "Neuropilin is a Receptor for the Axonal Chemorepellent Semaphorin III", *Cell* 90:739–751, 1997.

Kameyama, T., et al., "Identification of Plexin Family Molecules in Mice", *Biochemical and Biophysical Research Communications* 226:396–402, 1996.

Kameyama, T., et al., "Identification of a Neuronal Cell Surface Molecule, Plexin, in Mice", *Biochemical and Biophysical Research Communications* 226:524–529, 1996.

Kolodkin, A., et al., "The Semaphorin Genes Encode a Family of Transmembrane and Secreted Growth Cone Guidance Molecules", *Cell* 75:1389–1399, 1993.

Kolodkin, A. L., "Semaphorins: mediators of repulsive growth cone guidance", *Trends in Cell Biology* 6: 15–22, 1996.

Kolodkin, A. L., et al., "Neuropilin is a Semaphorin III Receptor", *Cell* 90:753–762, 1997.

Maestrini, E., et al., "A family of transmembrane proteins with homology to the MET–hepatocyte growth factor receptor", *Proc. Natl. Acad. Sci. USA* 93:674–678, 1996.

Mangasser–Stephan, K., et al., "Identification of Human Semaphorin E Gene Expression in Rheumatoid Synovial Cells by mRNA Differential Display", *Biochemical and Biophysical Research Communications* 234:153–156, 1997.

Nagase, T., et al., "Prediction of the Coding Sequences of Unidentified Human Genes. VII. The Complete Sequences of 100 New cDNA Clones from Brain Which Can Code for Large Proteins in Vitro", *DNA Research* 4:141–150, 1997.

Ohta, K., et al., "Plexin: A Novel Neuronal Cell Surface Molecule that Mediates Cell Adhesion via a Homophilic Binding Mechanism in the Presence of Calcium Ions", *Neuron* 14:1189–1199, 1995.

Promega Protein Guide: Tips and Techniques, Promega Corporation, Madison, WI, USA, 55–66, 1993.

Satoda, M., et al., "Differential Expression of Two Cell Surface Proteins, Neuropilin and Plexin, in Xenopus Olfactory Axon Subclasses", *Journal of Neuroscience* 15:942–955, 1995.

Tessier–Lavigne, M., et al., "The Molecular Biology of Axon Guidance", *Science* 274:1123–1133, 1996.

Trinchieri, G., et al., "Immunoregulation by interleukin–12", *Journal of Leukocyte Biology* 59:505–511, 1996.

*Primary Examiner*—Yvonne Eyler
*Assistant Examiner*—Nirmal S. Basi
(74) *Attorney, Agent, or Firm*—Kathleen Fowler; Simone L. Jones; Janis C. Henry

(57) ABSTRACT

The invention is directed to VESPR polypeptides as a purified and isolated protein, the DNA encoding the VESPR polypeptide, host cells transfected with cDNAs encoding VESPR, and methods for preparing VESPR polypeptides.

27 Claims, No Drawings

VIRAL ENCODED SEMAPHORIN PROTEIN RECEPTOR POLYPEPTIDES

This application is a divisional of U.S. Ser. No. 09/181,706, filed Oct. 28, 1998, now issued as U.S. Pat. No. 6,130,068, which is a continuation of U.S. Ser. No. 08/958,598, filed Oct. 28, 1997; converted to a provisional application U.S. Ser. No. 60/112,009, on Oct. 26, 1998, now abandoned.

FIELD OF THE INVENTION

The present invention relates to semaphorin receptor polypeptides, the nucleic acids encoding such semaphorin receptor polypeptides, processes for producing recombinant semaphorin receptor polypeptides, and pharmaceutical compositions containing such polypeptides.

BACKGROUND OF THE INVENTION

The semaphorin gene family includes a large number of molecules that encode related transmembrane and secreted glycoproteins known to be neurologic regulators. The semaphorins are generally well conserved in their extracellular domains which are typically about 500 amino acids in length. Semaphorin family proteins have been observed in neuronal and nonneuronal tissue and have been studied largely for their role in neuronal growth cone guidance. For example, the secreted semaphorins known as collapsin-1 and Drosophila semaphorin II are selectively involved in repulsive growth cone guidance during development. Flies having semaphorin II genes that are mutated so that their function is reduced exhibit abnormal behavior characteristics.

Another semaphorin gene has been identified in several strains of poxvirus. This semaphorin is found in vaccinia virus (Copenhagen strain) and is encoded in an open reading frame (ORF) known as A39R. The A39R encoded protein has no transmembrane domain and no potential membrane linkage and is known to be a secreted protein. A variola virus ORF also contains sequences that share homology with the vaccinia virus ORF A39R at the nucleotide level and the amino acid level. Another viral semaphorin, AHV-sema, has been found in the Alcelaphine Herpesvirus (AHV).

Genes encoding mammalian (human, rat, and mouse) semaphorins have been identified, based upon their similarity to insect semaphorins. Functional studies of these semaphorins suggest that embryonic and adult neurons require a semaphorin to establish workable connections. Significantly, the fast response time of growth cone cultures to appropriate semaphorins suggests that semaphorin signaling involves a receptor-mediated signal transduction mechanism. To date, one semaphorin receptor, designated neuropilin, has been isolated using mRNA from rat spinal cord. Another receptor, designated neuropilin-2, has been suggested (Kolodkin et al. *Cell* 90:753–762, 1997)

Semaphorin ligands that are secreted into the extracellular milieu signal through receptor bearing cells in a local and systemic fashion. In order to further investigate the nature of cellular processes regulated by such local and systemic signaling, it would be beneficial to identify additional semaphorin receptors and ligands. Furthermore, because virus encoded semaphorins are produced by infected cells and are present in viruses that are lytic (poxviruses) and viruses that are not known to be neurotropic (AHV), it is unlikely that their primary function is to modify neurologic responses. It is more likely that the virus encoded semaphorins function to modify the immunologic response of the infected host and it is likely that mammalian homologues to virus encoded semaphorins function to modify the immunologic response. In view of the suggestion that viral semaphorins may function in the immune system as natural immunoregulators it would be beneficial to identify semaphorin receptors as therapeutic agents for enhancing or downregulating the immune response.

SUMMARY OF THE INVENTION

The present invention pertains to semaphorin receptors as isolated or homogeneous proteins. In particular, the present invention provides a semaphorin receptor polypeptide, designated VESPR (Viral Encoded Semaphorin Protein Receptor) that binds semaphorins, including, but not limited to, the A39R vaccinia semaphorin and AHV semaphorin. Also, within the scope of the present invention are DNAs encoding VESPR polypeptides and expression vectors that include DNA encoding VESPR polypeptides. The present invention also includes host cells that have been transfected or transformed with expression vectors that include DNA encoding a VESPR polypeptide, and processes for producing VESPR polypeptides by culturing such host cells under conditions conducive to expression. The present invention further includes antibodies directed against VESPR polypeptides.

Further within the scope of the present invention are processes for purifying or separating semaphorins or cells that express semaphorins to which the VESPR polypeptides of the present invention bind. Such processes include binding at least one VESPR polypeptide to a solid phase matrix and contacting a mixture containing a semaphorin polypeptide to which the VESPR polypeptide binds, or a mixture of cells expressing the semaphorin with the bound VESPR polypeptide, and then separating the contacting surface and the solution.

The present invention additionally provides processes for treating inflammation and inflammatory diseases. Such processes include administering a therapeutically effective amount of a soluble VESPR polypeptide to an human or other mammal afflicted with a disease associated with proinflammatory activity of a semaphorin ligand.

DETAILED DESCRIPTION OF THE INVENTION

The present invention provides novel semaphorin receptor polypeptides designated Viral Encoded Semaphorin Protein Receptor (VESPR), DNA encoding VESPR polypeptides and recombinant expression vectors that include DNA encoding VESPR polypeptides. The present invention additionally provides methods for isolating VESPR polypeptides and methods for producing recombinant VESPR polypeptides by cultivating host cells transfected with the recombinant expression vectors under conditions appropriate for expressing semaphorin receptors and recovering the expressed receptor polypeptide.

In particular, the present invention provides VESPR polypeptides that bind semaphorins, including but not limited to, the vaccinia virus A39R semaphorin and the AHV semaphorin. The native VESPR polypeptide described herein was isolated using an Ectromelia virus A39R semaphorin/Fc fusion protein (A39RIFc) to recover VESPR from the membranes of human cells expressing the receptor. As described in the examples below, flow cytometry experiments establish that the VESPR polypeptide polypeptides of the present invention are expressed by B cells lines, monocyte-type cell lines, T cell lines, dendritic cells NK cells, lung epithelial cells, stroma, intestinal epithelial cells and lymphoma cells.

Furthermore, as demonstrated in the examples below, VESPR polypeptides of the present invention bind with their ligands to participate in upregulating the CD69 activation antigen on dendritic cells. Also characteristic of semaphorin receptors described herein is their ability to interact with their ligands to synergize with interferon and SAC to upregulate IL-12 production and down regulate MHC class II and CD86 expression on mouse dendritic cells. VESPR polypeptides of the present invention are also associated with increased expression of CD54 on monocytes which suggests cellular activation as a result of the interaction between semaphorins and their receptors. Among the uses of the VESPR polypeptides that flow from aforementioned biological properties of the receptor-ligand interaction are inducing IL-12 production and subsequent natural killer cell activation. VESPR polypeptide polypeptides find further use in treating diseases and adverse conditions associated with inflammation. In particular, soluble VESPR polypeptides can be used to antagonize proinflammatory activities associated with the interaction of semaphorin ligands and their receptors. Rheumatoid arthritis, a disease associated with chronic inflammation of synovial tissue,, has been linked with upregulation of the human semaphorin E gene (Mangasser-Stephan et al., *Biochem and Biophys Res Com,* 234:153–156, 1997). Thus, soluble forms of VESPR polypeptides of the present invention may be useful in downregulating semaphorin activity that mediates this inflammatory disease.

VESPR, a native semaphorin receptor of the present invention was isolated using a viral semaphorin ligand known as Ectromelia A39R. Example 1 below describes isolating the A39R semaphorin ligand and preparing an A39R/Fc fusion protein which was used to identify cell lines that bind the ligand and to determine the effects of interactions between A39R and its cell bound receptor.

Examples 4 and 5 describe identifying a native VESPR polypeptide of the present invention and isolating and purifying a human VESPR polypeptide. The amino acid sequence of the human VESPR polypeptide, isolated as described in Example 5, is disclosed in SEQ ID NO:2. The amino acid sequence of SEQ ID NO: 2 was obtained by sequencing the isolated and purified receptor using tandem mass spectrometry analysis of peptides produced in a trypsin digestion, in combination with contiguous EST sequences and identified cDNAs. The amino acid sequence presented in SEQ ID NO:2 has a predicted extracellular domain of amino acids 1–944 that includes a signal peptide with a cleavage site predicted at amino acid 34. The predicted transmembrane domain of SEQ ID NO:2 includes amino acids 945–965 and the cytoplasmic domain of SEQ ID NO:2 extends from amino acids 966-1568.

A DNA encoding amino acids 19–1100 of human VESPR in *E. coli* DH10B was deposited with the American type Culture Collection, 10801 University Boulevard, Manassas, Va., USA on Oct. 22, 1997 and assigned accession number 98560. The deposit was made under the terms of the Budapest Treaty. The DNA construct of the deposit differs from that of SEQ ID NO: 1 in that nucleotide 172 is C. The resulting encoded amino acid 58 is leu.

Amino acid sequence searches were performed in available data bases for proteins and polypeptides sharing homology with the full length VESPR or domains thereof. The searches for polypeptides sharing homology with VESPR were performed using the BLAST algorithm described by Altschul et al., *J Mol Bio* 215:403–410 (1990). This program was used to compare the VESPR amino acid sequence with protein and DNA sequences found in data bases obtained from the National Center for Biotechnology Information. Similarity scores obtained as a result of these searches identified groups of polypeptides having varying degrees of homology with VESPR. The highest degree of similarity was found to be between the VESPR and a group of proteins known as the "plexin gene family" (Maestrini et al., 1996, and Kameyama et al., 1996). Pairwise and multiple sequence alignments between VESPR and human and murine members of the plexin family were performed using the Smith-Waterman algorithm as implemented in the Genetics Computer Group (GCG) programs "BESTFIT" and "PILEUP" (Wisconsin Package, 9.0). The GCG program "DISTANCES" was used to calculate average pairwise percentage identity of the aligned protein sequences.

Pairwise sequence alignments between the VESPR polypeptide and each of several members of the plexin gene family revealed an average identity in their cytoplasmic domain (amino acids 966–1568) of 39% to 40% and an average identity for each of the entire protein of 24%–25%. The higher degree of homology in the cytoplasmic domains suggests similar signal transduction mechanisms among the cytoplasmic domains.

In order to identify regions of similarity between the protein sequences found to have some overall homology, homology analyses of the results of protein data base searches were performed using the BLIXEM and MSPCRUNCH programs (Sonnhammer and Durbin (1944a, b) The homology analyses revealed a novel subdomain with similarity to a region of the semaphorin domain of a number of members of the semaphorin family of genes described by Kolodkin et al. (1993). The novel subdomain includes amino acids 380–482 of the VESPR sequence of the present invention. This subdomain can be subdivided into two distinct smaller regions, that include residues 388–402 and 454–482, respectively. The C-proximal half-subdomain contains several highly conserved cysteine and tryptophan residues, forming a consensus sequence of C-x(5)-C-x(2)-C-x(7)-C-x-W-C-x(5)-C, where x is any amino acid. This entire subdomain is distinct from the canonical semaphorin domain described for the semaphorin gene family in that (a) it is smaller (100 amino acid residues for the subdomain vs 500 residues for the entire semaphorin domain), (b) it is also present in the plexin gene family and MET-hepatocyte growth factor receptor family, neither of which is a canonical semaphorin gene family members, and (c). it is present in a gene which is not itself a member of the semaphorin gene family but which interacts with a member of the semaphorin family (A39R). These subdomain sequences, therefore, represent peptides that are potentially capable of further identifying other receptors which interact with semaphorins.

A cDNA sequence that encodes the VESPR polypeptide of SEQ ID NO:2 was assembled as a composite of contiguous EST and cloned cDNA nucleotide sequences and is disclosed in SEQ ID NO: 1. As described in Example 5, identifying the cDNA that encodes the amino acid sequence of SEQ ID NO:2 enables constructing expression vectors that include the encoding cDNAs. Then culturing host cells transfected with a recombinant expression vector that contains cDNA encoding VESPR polypeptide, under conditions appropriate for expressing the VESPR polypeptide, and recovering the expressed VESPR polypeptide provides methods for producing VESPR polypeptides of the present invention.

Since VESPR polypeptide is found in B cell lines, T cell lines and dendritic cells, treating a variety of conditions associated with overactive or underactive immunoregulation is possible. Moreover, the ligand and receptor complex may be involved in neural growth, development and/or maintenance. While not limited to such, particular uses of the VESPR are described infra.

The terms "VESPR" and "VESPR polypeptide" of the present invention encompass polypeptides having the amino acid sequence SEQ ID NO:2, and proteins that are encoded by nucleic acids that contain the nucleic acid sequence of SEQ ID NO: 1. In addition, the terms include those polypeptides that have a high degree of similarity or a high degree of identity with the amino acid sequence of SEQ ID NO:2, which polypeptides are biologically active and bind at least one molecule or fragments of a molecule that are members of the semaphorin family. In addition, the term VESPR refers to biologically active gene products of the DNA of SEQ ID NO:1.

Further encompassed by the term VESPR are soluble or truncated proteins that comprise primarily the binding portion of the protein, retain biological activity and are capable of being secreted. Specific examples of such soluble proteins are those comprising the sequence of amino acids 1–944 of SEQ ID NO:2.

The term "biologically active" as it refers to VESPR or semaphorin receptor polypeptide, means that the VESPR or semaphorin receptor polypeptide is capable of binding to at least one semaphorin. Assays suitable for determining VESPR binding are described herein and can include standard flow cytometry tests and slide binding tests.

"Isolated" means a VESPR is substantially free of association with other proteins or polypeptides residual of the expression process, for example, as a purification product of recombinant host cell culture or as a purified extract.

A VESPR variant as referred to herein, means a polypeptide substantially homologous to native VESPR, but which has an amino acid sequence different from that of native VESPR because of one or more deletions, insertions or substitutions. The variant amino acid sequence preferably is at least 80% identical to a native VESPR amino acid sequence, most preferably at least 90% identical. The percent identity may be determined, for example, by comparing sequence information using the GAP computer program, version 8.1 described by Devereux et al. (*Nucl. Acids Res.* 12:387, 1984) and available from the University of Wisconsin Genetics Computer Group (UWGCG). The preferred default parameters for the GAP program include: (1) a unary comparison matrix (containing a value of 1 for identities and 0 for non-identities) for nucleotides, and the weighted comparison matrix of Gribskov and Burgess, *Nucl. Acids Res.* 14:6745, 1986, as described by Schwartz and Dayhoff, eds., *Atlas of Protein Sequence and Structure*, National Biomedical Research Foundation, pp. 353–358, 1979; (2) a penalty of 3.0 for each gap and an additional penalty for each symbol in each gap; and (3) no penalty for end gaps. Variants may comprise conservatively substituted sequences, meaning that a given amino acid residue is replaced by a residue having similar physiochemical characteristics. Examples of conservative substitutions include substitution of one aliphatic residue for another, such as Ile, Val, Leu, or Ala for one another, or substitutions of one polar residue for another, such as between Lys and Arg; Glu and Asp; or Gln and Asn. Other such conservative substitutions, for example, substitutions of entire regions having similar hydrophobicity characteristics, are well known. Naturally occurring VESPR variants or alleles are also encompassed by the invention. Examples of such variants are proteins that result from alternate niRNA splicing events or from proteolytic cleavage of the VESPR protein, wherein the binding property is retained. Alternate splicing of MRNA may yield a truncated but biologically active VESPR polypeptide, such as a naturally occurring soluble form of the protein, for example. Variations attributable to proteolysis include, for example, differences in the N-termini upon expression in different types of host cells, due to proteolytic removal of one or more terminal amino acids from the VESPR polypeptide (generally from 1–5 terminal amino acids).

As mentioned above, Example 1 describes the construction of novel viral A39R/Fc fusion proteins useful in studying VESPR binding. Other antibody Fc regions may be substituted for the human IgG1 Fc region described in the Example;. Suitable Fc regions are those that can bind with high affinity to protein A or protein G, and include the Fc region of human IgG1 or fragments of the human or murine IgG1 Fc region, e.g., fragments comprising at least the hinge region so that interchain disulfide bonds will form. The viral A39R:Fc fusion protein offers the advantage of being easily purified. In addition, disulfide bonds form between the Fc regions of two separate fusion protein chains, creating dimers.

As described above, in one aspect, the present invention includes soluble VESPR polypeptides. Soluble VESPR polypeptides comprise all or part of the extracellular domain of a native VESPR but lack the transmembrane region that would cause retention of the polypeptide on a cell membrane. Soluble VESPR polypeptides advantageously comprise the native (or a heterologous) signal peptide when initially synthesized to promote secretion, but the signal peptide is cleaved upon secretion of VESPR polypeptides from the cell. Soluble VESPR polypeptides encompassed by the invention retain the ability to bind semaphorin ligands. Indeed, soluble VESPR polypeptides may also include part of the signal or part of the cytoplasmic domain or other sequences, provided that the soluble VESPR protein can be secreted.

Soluble VESPR may be identified (and distinguished from its non-soluble membrane-bound counterparts) by separating intact cells which express the desired protein from the culture medium, e.g., by centrifugation, and assaying the medium (supernatant) for the presence of the desired protein. The presence of VESPR in the medium indicates that the protein was secreted from the cells and thus is a soluble form of the desired protein.

Soluble forms of VESPR polypeptides possess many advantages over the native, membrane bound VESPR protein. Purification of the proteins from recombinant host cells is feasible, since the soluble proteins are secreted from the cells. Further, soluble proteins are generally more suitable for intravenous administration.

Examples of soluble VESPR polypeptides include those comprising a substantial portion of the extracellular domain of a native VESPR polypeptide. An example of a soluble VESPR polypeptide is amino acids 1–944 of SEQ ID NO:2. In addition, truncated soluble VESPR proteins comprising less than the entire extracellular domain are included in the invention, e.g. amino acids 35–944. When initially expressed within a host cell, soluble VESPR polypeptides may additionally comprise one of the heterologous signal peptides described below that is functional within the host cells employed. Alternatively, the protein may comprise the native signal peptide. In one embodiment of the invention, soluble VESPR can be expressed as a fusion protein comprising (from N- to C-terminus) the yeast α-factor signal peptide, a FLAG® peptide described below and in U.S. Pat. No. 5,011,912, and soluble VESPR polypeptide consisting of amino acids 1–944 or 35–944 of SEQ ID NO:2. This recombinant fusion protein is expressed in and secreted from yeast cells. The FLAG® peptide facilitates purification of the protein, and subsequently may be cleaved from the soluble VESPR using bovine mucosal enterokinase. Isolated DNA sequences encoding soluble VESPR proteins are encompassed by the invention.

Truncated VESPR polypeptides, including soluble polypeptides, may be prepared by any of a number of conventional techniques. A desired DNA sequence may be chemically synthesized using techniques known per se. DNA fragments also may be produced by restriction endonuclease digestion of a full length cloned DNA sequence, and isolated by electrophoresis on agarose gels. Linkers containing restriction endonuclease cleavage site(s) may be employed to insert the desired DNA fragment into an expression vector, or the fragment may be digested at cleavage sites naturally present therein. The well known polymerase chain reaction procedure also may be employed to amplify a DNA sequence encoding a desired protein fragment. As a further alternative, known mutagenesis techniques may be employed to insert a stop codon at a desired point, e.g., immediately downstream of the codon for the last amino acid of the binding domain.

As stated above, the invention provides isolated or homogeneous VESPR polypeptides, both recombinant and non-recombinant. Variants and derivatives of native VESPR proteins that retain the desired biological activity (e.g., the ability to bind to semaphorins) may be obtained by mutations of nucleotide sequences coding for native VESPR polypeptides. Alterations of the native amino acid sequence may be accomplished by any of a number of conventional methods. Mutations can be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures can be employed to provide an altered gene wherein predetermined codons can be altered by substitution, deletion or insertion. Exemplary methods of making the alterations set forth above are disclosed by Walder et al. (*Gene* 42:133, 1986); Bauer et al. (*Gene* 37:73, 1985); Craik (*BioTechniques, January* 1985, 12–19); Smith et al. (*Genetic Engineering: Principles and Methods*, Plenum Press, 1981); Kunkel (*Proc. Natl. Acad. Sci. USA* 82:488, 1985); Kunkel et al. (*Methods in Enzymol.* 154:367, 1987); and U.S. Pat. Nos. 4,518,584 and 4,737,462 all of which are incorporated by reference.

Native VESPR polypeptide may be modified to create VESPR derivatives by forming covalent or aggregative conjugates with other chemical moieties, such as glycosyl groups, lipids, phosphate, acetyl groups and the like. Covalent derivatives of VESPR polypeptides may be prepared by linking the chemical moieties to functional groups on VESPR amino acid side chains or at the N-terminus or C-terminus of a VESPR polypeptide or the extracellular domain thereof. Other derivatives of VESPR polypeptides within the scope of this invention include covalent or aggregative conjugates of VESPR polypeptides or its fragments with other proteins or polypeptides, such as by synthesis in recombinant culture as N-terminal or C-terminal fusions. For example, the conjugate may comprise a signal or leader polypeptide sequence (e.g. the α-factor leader of Saccharomyces) at the N-terminus of a VESPR polypeptide. The signal or leader peptide co-translationally or post-translationally directs transfer of the conjugate from its site of synthesis to a site inside or outside of the cell membrane or cell wall.

VESPR polypeptide fusions can comprise peptides added to facilitate purification and identification of VESPR. Such peptides include, for example, poly-His or the antigenic identification peptides described in U.S. Pat. No. 5,011,912 and in Hopp et al., *Bio/Technology* 6:1204, 1988.

The invention further includes VESPR with or without associated native-pattern glycosylation. VESPR polypeptide expressed in yeast or mammalian expression systems (e.g., COS-7 cells) may be similar to or significantly different from a native VESPR polypeptide in molecular weight and glycosylation pattern, depending upon the choice of expression system. Expression of VESPR polypeptides in bacterial expression systems, such as *E. coli*, provides non-glycosylated molecules.

Equivalent DNA constructs that encode various additions or substitutions of amino acid residues or sequences, or deletions of terminal or internal residues or sequences not needed for biological activity or binding are encompassed by the invention. For example, N-glycosylation sites in the VESPR extracellular domain can be modified to preclude glycosylation, allowing expression of a reduced carbohydrate analog in mammalian and yeast expression systems. N-glycosylation sites in eukaryotic polypeptides are characterized by an amino acid triplet Asn-X-Y, wherein X is any amino acid except Pro and Y is Ser or Thr. The native human VESPR protein comprises 24 such triplets, at amino acids 86–88, 141–143, 149–151, 241–243, 252–254, 386–388, 407–409, 548–550, 553–555, 582–584, 588–590, 591–593, 653,655, 686–688, 692–694, 715–717, 741–743, 771–773, 796–798, 821–823, 871–873, 890–892, 895–897 and 920–922 of SEQ ID NO:2. Appropriate substitutions, additions or deletions to the nucleotide sequence encoding these triplets will result in prevention of attachment of carbohydrate residues at the Asn side chain. Alteration of a single nucleotide, chosen so that Asn is replaced by a different amino acid, for example, is sufficient to inactivate an N-glycosylation site. Known procedures for inactivating N-glycosylation sites in proteins include those described in U.S. Pat. No. 5,071,972 and EP 276,846, hereby incorporated by reference.

In another example, sequences encoding Cys residues that are not essential for biological activity can be altered to cause the Cys residues to be deleted or replaced with other amino acids, preventing formation of incorrect intramolecular disulfide bridges upon renaturation. Other equivalents are prepared by modification of adjacent dibasic amino acid residues to enhance expression in yeast systems in which KEX2 protease activity is present. EP 212,914 discloses the use of site-specific mutagenesis to inactivate KEX2 protease processing sites in a protein. KEX2 protease processing sites are inactivated by deleting, adding or substituting residues to alter Arg—Arg, Arg-Lys, and Lys-Arg pairs to eliminate the occurrence of these adjacent basic residues. Lys—Lys pairings are considerably less susceptible to KEX2 cleavage, and conversion of Arg-Lys or Lys-Arg to Lys—Lys represents a conservative and preferred approach to inactivating KEX2 sites. The human VESPR contains 11 KEX2 protease processing sites Nucleic acid sequences within the scope of the invention include isolated DNA and RNA sequences that hybridize to the VESPR nucleotide sequences disclosed herein under conditions of moderate or high stringency, and that encode biologically active VESPR. Conditions of moderate stringency, as defined by Sambrook et al. *Molecular Cloning: A Laboratory Manual*, 2 ed. Vol. 1, pp. 101–104, Cold Spring Harbor Laboratory Press, (1989), include use of a prewashing solution of 5 X SSC, 0.5% SDS, 1.0 mM EDTA (pH 8.0) and hybridization conditions of about 55° C., 5 X SSC, overnight. Conditions of high stringency include higher temperatures of hybridization and washing. The skilled artisan will recognize that the temperature and wash solution salt concentration may be adjusted as necessary according to factors such as the length of the nucleic acid molecule and the relative amount of A, T/U, C and G nucleotides.

Due to the known degeneracy of the genetic code wherein more than one codon can encode the same amino acid, a DNA sequence may vary from that shown in SEQ ID NO:1 and still encode a VESPR polypeptide having the amino acid sequence of SEQ ID NO:2. Such variant DNA sequences may result from silent mutations (e.g., occurring during PCR amplification), or may be the product of deliberate mutagenesis of a native sequence.

The invention provides equivalent isolated DNA sequences encoding biologically active VESPR, selected from: (a) cDNA comprising the nucleotide sequence presented in SEQ ID NO:1; (b) DNA capable of hybridization to a DNA of (a) under moderately stringent conditions and that encodes biologically active VESPR polypeptide; (c) DNA that is degenerate as a result of the genetic code to a DNA defined in (a) or (b) and that encodes biologically active VESPR polypeptide; and (d) DNA complementary to the DNA of (a), (b) or (c). VESPR polypeptides encoded by such DNA equivalent sequences are encompassed by the invention.

DNAs that are equivalents to the DNA sequence of SEQ ID NO:1 will hybridize under moderately and highly stringent conditions to the DNA sequence that encodes polypeptides comprising the sequence of SEQ ID NO:2. Examples of VESPR proteins encoded by such DNA, include, but are not limited to, VESPR fragments and VESPR proteins comprising inactivated N-glycosylation site(s), inactivated KEX2 protease processing site(s), or conservative amino acid substitution(s), as described above. VESPR polypeptides encoded by DNA derived from other species, wherein the DNA will hybridize to the cDNA of SEQ ID NO:1 are also encompassed.

Variants possessing the requisite ability to bind semaphorins may be identified by any suitable assay. Biological activity of VESPR polypeptides may be determined, for example, by competition for binding to the receptor binding domain of semaphorins (i.e. competitive binding assays).

One type of a competitive binding assay for a VESPR polypeptide uses a radiolabeled, soluble VESPR and intact semaphorin-expressing cells. Instead of intact cells, one could substitute soluble semaphorin:Fc fusion proteins bound to a solid phase through the interaction of a Protein A, Protein G or an antibody to the semaphorin or Fc portions of the molecule, with the Fc region of the fusion protein. Another type of competitive binding assay utilizes radiolabeled soluble semaphorins such as a fusion protein, and intact cells expressing VESPR.

Competitive binding assays can be performed following conventional methodology. In one embodiment, a soluble VESPR polypeptide can be made to compete with an immobilized receptor for binding with a soluble semaphorin ligand. For example, a radiolabeled soluble semaphorin ligand can be antagonized by soluble VESPR in an assay for binding activity against a surface-bound semaphorin receptor. Qualitative results can be obtained by competitive autoradiographic plate binding assays, or Scatchard plots may be utilized to generate quantitative results.

Alternatively, semaphorin binding proteins, such as VESPR or anti-semaphorin antibodies, can be bound to a solid phase such as a column chromatography matrix or a similar substrate suitable for identifying, separating or purifying cells that express semaphorin on their surface. Binding of a semaphorin-binding protein to a solid phase contacting surface can be accomplished by any means, for example, by constructing a VESPR:Fc fusion protein and binding such to the solid phase through the interaction of Protein A or Protein G. Various other means for fixing proteins to a solid phase are well known in the art and are suitable for use in the present invention. For example, magnetic microspheres can be coated with VESPR and held in the incubation vessel through a magnetic field. Suspensions of cell mixtures containing semaphorin-expressing cells are contacted with the solid phase that has VESPR polypeptides thereon. Cells having semaphorin on their surface bind to the fixed VESPR and unbound cells then are washed away. This affinity-binding method is useful for purifying, screening or separating such semaphorin-expressing cells from solution. Methods of releasing positively selected cells from the solid phase are known in the art and encompass, for example, the use of enzymes. Such enzymes are preferably non-toxic and non-injurious to the cells and are preferably directed to cleaving the cell-surface binding partner. In the case of semaphorin-VESPR interactions, the enzyme preferably would cleave the semaphorin, thereby freeing the resulting cell suspension from the "foreign" semaphorin receptor material. The purified cell population then may be used to repopulate mature (adult) tissues.

Alternatively, mixtures of cells suspected of containing semaphorin-positive cells first can be incubated with biotinylated VESPR. Incubation periods are typically at least one hour in duration to ensure sufficient binding to semaphorin The resulting mixture then is passed through a column packed with avidin-coated beads, whereby the high affinity of biotin for avidin provides the binding of the cell to the beads. Use of avidin-coated beads is known in the art. See Berenson, et al. *J. Cell Biochem.*, 10D:239 (1986). Washing unbound material and releasing the bound cells is performed using conventional methods.

As described above, VESPR can be used to separate cells expressing semaphorin. In an alternative method, VESPR or an extracellular domain or a fragment thereof can be conjugated to a detectable moiety such as $^{125}I$ to detect semaphorin-expressing cells. Radiolabeling with $^{125}I$ can be performed by any of several standard methodologies that yield a functional $^{125}I$-VESPR molecule labeled to high specific activity. Or an iodinated or biotinylated antibody against the semaphorin receptor can be used. Another detectable moiety such as an enzyme that can catalyze a colorimetric or fluorometric reaction, biotin or avidin may be used. Cells to be tested for semaphorin-expression can be contacted with labeled VESPR polypeptide. After incubation, unbound labeled VESPR is removed and binding is measured using the detectable moiety.

The binding characteristics of VESPR (including variants) may also be determined using a conjugated semaphorin (for example, $^{125}I$-semaphorin:Fc) in competition assays similar to those described above. In this case, however, intact cells expressing semaphorins bound to a solid substrate are used to measure the extent to which a sample containing a putative VESPR variant competes for binding with a conjugated semaphorin.

Other means of assaying for VESPR include the use of anti-VESPR antibodies, cell lines that proliferate in response to VESPR, or recombinant cell lines that express semaphorin and proliferate in the presence of VESPR.

The VESPR proteins disclosed herein also may be employed to measure the biological activity of semaphorin proteins in terms of their binding affinity for VESPR. As one example, VESPR polypeptides of the present invention may be used in determining whether biological activity is retained after modification of a semaphorin protein (e.g., chemical modification, truncation, mutation, etc.). The biological activity of a semaphorin protein thus can be ascertained before it is used in a research study, or in the clinic, for example.

VESPR polypeptides of the present invention find use as reagents that may be employed by those conducting "quality assurance" studies, e.g., to monitor shelf life and stability of semaphorin protein under different conditions. To illustrate, VESPR polypeptides may be employed in a binding affinity study to measure the biological activity of an semaphorin protein that has been stored at different temperatures, or produced in different cell types. The binding affinity of the modified semaphorin protein for VESPR is compared to that of an unmodified semaphorin protein to detect any adverse impact of the modifications on biological activity of the semaphorin.

VESPR polypeptides also find use as carriers for delivering agents attached thereto to cells expressing semaphorins. As described in example 7 below, a putative human semaphorin is expressed in cells found in the placenta, testis, ovary and spleen. VESPR polypeptides can thus can be used to deliver diagnostic or therapeutic agents to these cells (or to other cell types found to express a semaphorin on a cell surfaces) in in vitro or in vivo procedures.

Diagnostic and therapeutic agents that may be attached to a VESPR polypeptide include. but are not limited to, drugs, toxins, radionuclides, chromophores, enzymes that catalyze a calorimetric or fluorometric reaction, and the like, with the particular agent being chosen according to the intended application. Examples of drugs include those used in treating various forms of cancer, e.g., nitrogen mustards such as L-phenylalanine nitrogen mustard or cyclophosphamide, intercalating agents such as cis-diaminodichloroplatinum, antimetabolites such as 5-fluorouracil, vinca alkaloids such as vincristine, and antibiotics such as bleomycin, doxorubicin, daunorubicin, and derivatives thereof. Among the toxins are ricin, abrin, diptheria toxin, *Pseeudomonas aeruginosa* exotoxin A, ribosomal inactivating proteins, mycotoxins such as trichothecenes, and derivatives and fragments (e.g., single chains) thereof. Radionuclides suitable for diagnostic use include, but are not limited to, $^{123}I$, $^{131}I$, $^{99m}Tc$, $^{111}In$, and $^{76}Br$. Radionuclides suitable for therapeutic use include, but are not limited to, $^{131}I$, $^{211}At$, $^{77}Br$, $^{186}Re$, $^{188}Re$, $^{212}Pb$, $^{212}Bi$, $^{109}Pd$, $^{64}Cu$, and $^{67}Cu$.

Such agents may be attached to the semaphorin receptor by any suitable conventional procedure. VESPR, being a protein, comprises functional groups on amino acid side chains that can be reacted with functional groups on a desired agent to form covalent bonds, for example. Alternatively, the protein or agent may be derivatized to generate or attach a desired reactive functional group. The derivatization may involve attachment of one of the bifunctional coupling reagents available for attaching various molecules to proteins (Pierce Chemical Company, Rockford, Ill.). A number of techniques for radiolabeling proteins are known. Radionuclide metals may be attached to the receptor by using a suitable bifunctional chelating agent, for example.

Conjugates comprising VESPR and a suitable diagnostic or therapeutic agent (preferably covalently linked) are thus prepared. The conjugates are administered or otherwise employed in an amount appropriate for the particular application.

Another use of the VESPR of the present invention is as a research tool for studying the role that the receptor, in conjunction with semaphorins, may play in immune regulation and viral infection. The VESPR polypeptides of the present invention also may be employed in in vitro assays for detection of semaphorin to which it binds or VESPR, or the interactions thereof.

As described in Example 16 semaphorins interact with their membrane bound receptors of the present invention to synergize with interferon and Staphylococcus aureus (type C) (SAC) in the production of IL-12 from dendritic cells. The use of VESPR and its semaphorin ligand to induce L-12 production promotes natural killer cell and T cell production and induces cytokine production (primarily γ-interferon). IL-12 and IL-12 induced y interferon production favors Thl cell differentiation, and downregulates the production of cytokines associated with Th2 cell differentiation. IL-12 is known to act as both a proinflammatory cytokine and an immunomodulator. Thus, a soluble VESPR can be used to antagonize IL-12 production and downregulate an organism's Thl cell differentiation. Similarly, a soluble VESPR can be used to promote production of cytokines associated with Th2 cell differentiation, thus discouraging proinflammatory activity. Also, VESPR in combination with its semaphorin ligand can be used to boost IL-12 production in combination with vaccination for those pathogens against which cellular immunity are effective. In this manner the enhanced amount of IL-12 acts as an adjuvant in the vaccination to induce a more persistent Th 1-type immunological memory.

Furthermore, it is known that administration of IL-12 to tumor bearing animals results in tumor regression and the establishment of a tumor-specific immune response. Thus, using a semaphorin ligand to bind with VESPR in order to enhance or promote IL-12 can induce a curative immune response against aggressive micrometastasizing tumors.

Additionally, as described in example 18, receptors of the present invention bind with their semaphorin ligands to increase CD54 expression on monocytes. This observation suggests that the semaphorin/semaphorin receptor interaction mediate cellular activation that contributes to the proinflammatory activity typically associated with monocyte activation. Such activity includes increased phagocytosis, pinocytosis, nitric oxide production and cytokine production. To antagonize or reverse the proinflammatory activity resulting from the interaction between the semaphorin ligand and its membrane bound receptor, a pharmaceutical composition containing a therapeutically effect amount of a soluble VESPR of the present invention can be administered parenterally to an organism. The soluble VESPR binds with the semaphorin ligand thus preventing the ligand from binding with a membrane bound receptor and contributing to the proinflammatory activity. A therapeutically effect amount of VESPR is an amount sufficient to antagonize proinflammatory activity.

Semaphorin ligands binding with VESPR to downregulate expression of MHC Class II molecules and CD86, a co-stimulatory molecule, on dendritic cells, cultured with GM-CSF and IL-4 (see example 17) suggests that the interaction between semaphorin ligands and the receptors of the present invention are associated with the immune suppression of mature dendritic cells. To antagonize or reverse the immunosuppression activity resulting from the interaction between the semaphorin ligand and its membrane bound receptor, a pharmaceutical composition containing a therapeutically effective amount of a soluble VESPR of the present invention can be administered parenterally to an organism. The soluble VESPR binds with the semaphorin ligand thus preventing the ligand from binding with a membrane bound receptor and contributing to the immunosuppression activity. Alternatively, in patients or organisms that suffer from the effects of chronic inflammation, administering appropriate semaphorin ligands will contribute to suppressing the proinflammatory activity of differentiated macrophages.

VESPR polypeptides of the invention can be formulated according to known methods used to prepare pharmaceutically useful compositions. VESPR can be combined in admixture, either as the sole active material or with other known active materials, with pharmaceutically suitable diluents (e.g., Tris-HCI, acetate, phosphate), preservatives (e.g., Thimerosal, benzyl alcohol, parabens), emulsifiers, solubilizers, adjuvants and/or carriers. Suitable carriers and their formulations are described in Remington's Pharmaceutical Sciences, 16th ed. 1980, Mack Publishing Co. In addition, such compositions can contain VESPR polypeptide complexed with polyethylene glycol (PEG), metal ions, or incorporated into polymeric compounds such as polyacetic acid, polyglycolic acid, hydrogels, etc., or incorporated into liposomes, microemulsions, micelles, unilamellar or multilamellar vesicles, erythrocyte ghosts or spheroblasts. Such compositions will influence the physical state, solubility, stability, rate of in vivo release, and rate of in vivo clearance of VESPR. VESPR polypeptide can also be conjugated to antibodies against tissue-specific receptors, ligands or antigens, or coupled to ligands of tissue-specific receptors.

VESPR polypeptides can be administered topically, parenterally, or by inhalation. The term "parenteral" includes subcutaneous injections, intravenous, intramuscular, intracisternal injection, or infusion techniques. These compositions will typically contain an effective amount of the VESPR, alone or in combination with an effective amount of any other active material. Such dosages and desired drug concentrations contained in the compositions may vary depending upon many factors, including the intended use, patient's body weight and age, and route of administration. Preliminary doses can be determined according to animal tests, and the scaling of dosages for human administration can be performed according to art-accepted practices.

VESPR polypeptides may exist as oligomers, such as covalently-linked or non-covalently-linked dimers or trimers. Oligomers may be linked by disulfide bonds formed between cysteine residues on different VESPR molecules. In one embodiment of the invention, a VESPR dimer is created by fusing VESPR to the Fc region of an antibody (e.g., IgG1) in a manner that does not interfere with binding of VESPR to a semaphorin ligand-binding domain. The Fc polypeptide preferably is fused to the C-terminus of a soluble VESPR (comprising only the ligand-binding domain). General preparation of fusion proteins comprising heterologous polypeptides fused to various portions of antibody-derived polypeptides (including the Fc domain) has been described, e.g., by Ashkenazi et al. (*PNAS USA* 88:10535, 1991) and Byrn et al. (*Nature* 344;677, 1990), hereby incorporated by reference. A gene fusion encoding the VESPR:Fc fusion protein is inserted into an appropriate expression vector. VESPR:Fc fusion proteins are allowed to assemble much like antibody molecules, whereupon interchain disulfide bonds form between Fc polypeptides, yielding divalent. If fusion proteins are made with both heavy and light chains of an antibody, it is possible to form a VESPR oligomer with as many as four VESPR extracellular regions. Alternatively, one can link two soluble VESPR domains with a peptide linker.

Suitable host cells for expression of VESPR polypeptides include prokaryotes, yeast or higher eukaryotic cells. Appropriate cloning and expression vectors for use with bacterial, fungal, yeast, and mammalian cellular hosts are described, for example, in Pouwels et al. *Cloning Vectors: A Laboratory Manual*, Elsevier, N.Y., (1985). Cell-free translation systems could also be employed to produce VESPR polypeptides using RNAs derived from DNA constructs disclosed herein. Prokaryotes include gram negative or gram positive organisms, for example, *E. coli* or Bacillus. Suitable prokaryotic host cells for transformation include, for example, *E. coli, Bacillus subtilis, Salmonella typhimurium*, and various other species within the genera Pseudomonas, Streptomyces, and Staphylococcus. In a prokaryotic host cell, such as *E. coli*, a VESPR polypeptide may include an N-terminal methionine residue to facilitate expression of the recombinant polypeptide in the prokaryotic host cell. The N-terminal methionine may be cleaved from the expressed recombinant VESPR polypeptide.

VESPR polypeptides may be expressed in yeast host cells, preferably from the Saccliaromyces genus (e.g., S. cerevisiae). Other genera of yeast, such as Pichia, *K. lactis* or Kluyveromyces, may also be employed. Yeast vectors will often contain an origin of replication sequence from a 2 μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., *J. Biol. Chem.* 255;2073, 1980) or other glycolytic enzymes (Hess et al., *J. Adv. Enzyme Reg.* 7:149, 1968; and Holland et al., Biochem. 17:4900, 1978), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Hitzeman, EPA-73,657 or in Fleer et. al., *Gene,* 107:285–195 (1991); and van den Berg et. al., *Bio/Technology,* 8:135–139 (1990). Another alternative is the glucose-repressible ADH2 promoter described by Russell et al. (*J. Biol. Chem.* 258:2674, 1982) and Beier et al. (*Nature* 300:724, 1982). Shuttle vectors replicable in both yeast and *E. coli* may be constructed by inserting DNA sequences from pBR322 for selection and replication in *E. coli* (Amp$^r$ gene and origin of replication) into the above-described yeast vectors.

The yeast α-factor leader sequence may be employed to direct secretion of the VESPR polypeptide. The α-factor leader sequence is often inserted between the promoter sequence and the structural gene sequence. See, e.g., Kurjan et al., *Cell* 30:933, 1982; Bitter et al., *Proc. Natl. Acad. Sci. USA* 81:5330, 1984; U.S. Pat. No. 4,546,082; and EP 324,274. Other leader sequences suitable for facilitating secretion of recombinant polypeptides from yeast hosts are known to those of skill in the art. A leader sequence may be modified near its 3' end to contain one or more restriction sites. This will facilitate fusion of the leader sequence to the structural gene.

Yeast transformation protocols are known to those of skill in the art. One such protocol is described by Hinnen et al., *Proc. Natl. Acad. Sci. USA* 75:1929, 1978. The Hinnen et al. protocol selects for Trp$^+$ transformants in a selective medium, wherein the selective medium consists of 0.67% yeast nitrogen base, 0.5% casamino acids, 2% glucose, 10 µg/ml adenine and 20 µg/ml uracil.

Yeast host cells transformed by vectors containing ADH2 promoter sequence may be grown for inducing expression in a "rich" medium. An example of a rich medium is one consisting of 1% yeast extract, 2% peptone, and 1% glucose supplemented with 80 µg/ml adenine and 80 µg/ml uracil. Depression of the ADH2 promoter occurs when glucose is exhausted from the medium.

Mammalian or insect host cell culture systems could also be employed to express recombinant VESPR polypeptides. Baculovirus systems for production of heterologous proteins in insect cells are reviewed by Luckow and Summers, *Bio/Technology* 6:47 (1988). Established cell lines of mammalian origin also may be employed. Examples of suitable mammalian host cell lines include the COS-7 line of monkey kidney cells (ATCC CRL 1651) (Gluzman et al., *Cell* 23:175, 1981), L cells, C127 cells, 3T3 cells (ATCC CCL 163), Chinese hamster ovary (CHO) cells, HeLa cells, and BHK (ATCC CRL 10) cell lines, and the CV-1/EBNA-1 cell line derived from the African green monkey kidney cell line CVI (ATCC CCL 70) as described by McMahan et al. (*EMBO J.* 10: 2821, 1991).

Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome, for example, SV40 origin, early and late promoter, enhancer, splice, and polyadenylation sites may be used to provide other genetic elements for expression of a structural gene sequence in a mammalian host cell. Viral early and late promoters are particularly useful because both are easily obtained from a viral genome as a fragment which may also contain a viral origin of replication (Fiers et al., *Nature* 273:113, 1978). Smaller or larger SV40 fragments may also be used, provided the approximately 250 bp sequence extending from the Hind III site toward the Bgl I site located in the SV40 viral origin of replication site is included.

Exemplary expression vectors for use in mammalian host cells can be constructed as disclosed by Okayama and Berg (*Mol. Cell. Biol.* 3:280, 1983). A useful system for stable high level expression of mammalian cDNAs in C127 murine mammary epithelial cells can be constructed substantially as described by Cosman et al. (*Mol. Immunol.* 23:935, 1986). A useful high expression vector, PMLSV N1IN4, described by Cosman et al., *Nature* 312:768, 1984 has been deposited as ATCC 39890. Additional useful mammalian expression vectors are described in EP-A-0367566, and in U.S. patent application Ser. No. 07/701,415, filed May 16, 1991, incorporated by reference herein. The vectors may be derived from retroviruses. In place of the native signal sequence, and in addition to an initiator methionine, a heterologous signal sequence may be added, such as the signal sequence for IL-7 described in U.S. Pat. No. 4,965,195; the signal sequence for IL-2 receptor described in Cosman et al., *Nature* 312:768 (1984); the IL-4 signal peptide described in EP 367,566; the type I IL-1 receptor signal peptide described in U.S. Pat. 4,968,607; and the type II IL-1 receptor signal peptide described in EP 460,846.

VESPR polypeptides as isolated, purified or homogeneous proteins according to the invention may be produced by recombinant expression systems as described above or purified from naturally occurring cells. VESPR can be purified to substantial homogeneity, as indicated by a single protein band upon analysis by SDS-polyacrylamide gel electrophoresis (SDS-PAGE).

One process for producing VESPR comprises culturing a host cell transformed with an expression vector comprising a DNA sequence that encodes VESPR polypeptide under conditions sufficient to promote expression of VESPR polypeptide. The receptor is then recovered from culture medium or cell extracts, depending upon the expression system employed. As is known to the skilled artisan, procedures for purifying a recombinant protein will vary according to such factors as the type of host cells employed and whether or not the recombinant protein is secreted into the culture medium.

For example, when expression systems that secrete the recombinant protein are employed, the culture medium first may be concentrated using a commercially available protein concentration filter, for example, an Amicon or Millipore Pellicon ultrafiltration unit. Following the concentration step, the concentrate can be applied to a purification matrix such as a gel filtration medium. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Sulfopropyl groups are preferred. Finally, one or more reversed-phase high performance liquid chromatography (RP-HPLC) steps employing hydrophobic RP-HPLC media, (e.g., silica gel having pendant methyl or other aliphatic groups) can be employed to further purify VESPR polypeptide. Some or all of the foregoing purification steps, in various combinations, are well known and can be employed to provide a substantially homogeneous recombinant protein.

It is possible to utilize an affinity column comprising the receptor-binding domain of a semaphorin that binds VESPR to affinity-purify expressed VESPR polypeptides. VESPR polypeptides can be removed from an affinity column using conventional techniques, e.g., in a high salt elution buffer and then dialyzed into a lower salt buffer for use or by changing pH or other components depending on the affinity matrix utilized. Alternatively, the affinity column may comprise an antibody that binds VESPR. Example 20 describes a procedure for employing VESPR of the invention to generate monoclonal antibodies directed against VESPR Recombinant protein produced in bacterial culture can be isolated by initial disruption of the host cells, centrifugation, extraction from cell pellets if an insoluble polypeptide, or from the supernatant fluid if a soluble polypeptide, followed by one or more concentration, salting-out, ion exchange, affinity purification or size exclusion chromatography steps. Finally, RP-HPLC can be employed for final purification steps. Microbial cells can be disrupted by any convenient method, including freeze-thaw cycling, sonication, mechanical disruption, or use of cell lysing agents.

Transformed yeast host cells are preferably employed to express VESPR as a secreted polypeptide in order to simplify purification. Secreted recombinant polypeptide from a yeast host cell fermentation can be purified by methods analogous to those disclosed by Urdal et al. (*J. Chromatog.* 296:171, 1984). Urdal et al. describe two sequential, reversed-phase HPLC steps for purification of recombinant human IL-2 on a preparative HPLC column.

Useful fragments of the VESPR nucleic acids include antisense or sense oligonucleotides comprising a single-stranded nucleic acid sequence (either RNA or DNA) capable of binding to target VESPR mRNA (sense) or VESPR DNA (antisense) sequences. Antisense or sense oligonucleotides, according to the present invention, comprise a fragment of the coding region of VESPR cDNA. Such a fragment generally comprises at least about 14 nucleotides, preferably from about 14 to about 30 nucleotides. The ability to derive an antisense or a sense oligonucleotide, based upon a cDNA sequence encoding a given protein is described in, for example, Stein and Cohen (*Cancer Res.* 48:2659, 1988) and van der Krol et al. (*BioTechniques* 6:958, 1988).

Binding of antisense or sense oligonucleotides to target nucleic acid sequences results in the formation of duplexes that block transcription or translation of the target sequence by one of several means, including enhanced degradation of the duplexes, premature termination of transcription or translation, or by other means. The antisense oligonucleotides thus may be used to block expression of VESPR proteins.

Antisense or sense oligonucleotides further comprise oligonucleotides having modified sugar-phosphodiester backbones (or other sugar linkages, such as those described in WO91/06629) and wherein such sugar linkages are resistant to endogenous nucleases. Such oligonucleotides with resistant sugar linkages are stable in vivo (i.e., capable of resisting enzymatic degradation) but retain sequence specificity to be able to bind to target nucleotide sequences. Other examples of sense or antisense oligonucleotides include those oligonucleotides which are covalently linked to organic moieties, such as those described in WO 90/10448, and other moieties that increases affinity of the oligonucleotide for a target nucleic acid sequence, such as poly-(L-lysine). Further still, intercalating agents, such as ellipticine, and alkylating agents or metal complexes may be attached to sense or antisense oligonucleotides to modify binding specificities of the antisense or sense oligonucleotide for the target nucleotide sequence.

Antisense or sense oligonucleotides may be introduced into a cell containing the target nucleic acid sequence by any gene transfer method, including, for example, CaPO$_4$-mediated DNA transfection, electroporation, or by using gene transfer vectors such as Epstein-Barr virus. Antisense or sense oligonucleotides are preferably introduced into a cell containing the target nucleic acid sequence by insertion of the antisense or sense oligonucleotide into a suitable retroviral vector, then contacting the cell with the retrovirus vector containing the inserted sequence, either in vivo or ex vivo. Suitable retroviral vectors include, but are not limited to, those derived from the murine retrovirus M-MuLV, N2 (a retrovirus derived from M-MuLV), or the double copy vectors designated DCT5A, DCT5B and DCT5C (see PCT Application US 90/02656).

Sense or antisense oligonucleotides also may be introduced into a cell containing the target nucleotide sequence by formation of a conjugate with a ligand binding molecule, as described in WO 91/04753. Suitable ligand binding molecules include, but are not limited to, cell surface receptors, growth factors, other cytokines, or other ligands that bind to cell surface receptors. Preferably, conjugation of the ligand binding molecule does not substantially interfere with the ability of the ligand binding molecule to bind to its corresponding molecule or receptor, or block entry of the sense or antisense oligonucleotide or its conjugated version into the cell.

Alternatively, a sense or an antisense oligonucleotide may be introduced into a cell containing the target nucleic acid sequence by formation of an oligonucleotide-lipid complex, as described in WO 90/10448. The sense or antisense oligonucleotide-lipid complex is preferably dissociated within the cell by an endogenous lipase.

In addition to the above, the following examples are provided to illustrate particular embodiments and not to limit the scope of the invention.

EXAMPLE 1

Preparing an Ectromelia Semaphorin/Fc Fusion Protein

The following describes preparation of an Ectromelia Semaphorin A39R/immunoglobulin fusion protein (A39R/Fc). The process included preparing a DNA construct that encodes the fusion protein, transfecting a cell line with the DNA construct, and harvesting supernatants from the transfected cells. The A39R/Fc fusion protein was used as described in Examples 3, 4, 5 and 6 to study VESPR binding characteristics and isolate VESPR.

DNA encoding A39R semaphorin was isolated and amplified from genomic Ectromelia virus DNA using PCR techniques and synthesized oligonucleotide primers whose sequences were based on published A39R sequences in the Copenhagen strain of Vaccinia Virus. The Copenhagen strain A39R DNA sequence is described in Goebel, S.J. et al. *Virology* 179:247, 1990. The isolated Ectromelia A39R DNA is presented in SEQ ID NO:7 and the protein encoded by the DNA is presented in SEQ ID NO:8. The upstream oligonucleotide primer introduced an SpeI site upstream of amino acid 15 of the A39R polypeptide. A downstream oligonucleotide primer introduced a NotI site downstream of the termination codon of Ectromelia A39R, after amino acid 399. The primer sequences were as follows:

```
Upstream SpeI primer:
TGTCACTAGT ATCGAATGGC ATAAGTTGA A        (SEQ ID NO:3)
    Spe 1          A39R DNA Downstream NotI primer:
GACAGCGGCC GC                            (SEQ ID NO:4)
CTATTACA TTTTAAGTAT TTT
    Not 1           A39R DNA
```

A Bgl II to Nsl I restriction fragment containing a mutein human Fc region of immunoglobulin as described by Baum et al. *Cir. Sh.* 44:30 (1994) was ligated into an expression vector (pDC304) containing a murine IL-7 signal peptide and a FLAG™ octapeptide as described in U.S. Pat. No. 5,011,912. The PCR amplified DNA encoding amino acids 15–399 of Ectromelia A39R was then ligated into the expression vector containing the mutein human Fc region, the murine IL-7 signal peptide and FLAG™ peptide, in a two way ligation. The resulting DNA construct was transfected into the monkey kidney cell lines CV-1/EBNA (with co-transfection of psv3neo). After 7 days of culture in medium containing 0.5% low immunoglobulin bovine serum, a solution of 0.2% azide was added to the supernatant and the supernatant was filtered through a 0.22 µm filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the PLC column with citric acid adjusted to pH 3.0. Eluted purified fusion protein was neutralized as it eluted using 1M HEPES solution at pH 7.4.

EXAMPLE 2

Preparing An Ectromelia Semaphorin/polyHis Fusion Protein

The following describes preparation of an Ectromelia A39R/polyHis fusion protein (A39R/polyHis). The process included preparing a DNA construct that encodes the fusion protein, transfecting a cell line with the DNA construct, and harvesting supernatants from the transfected cells., DNA encoding Ectromelia A39R (amino acids 1–399 of A39R ORF, SEQ ID NO:8) was isolated and amplified from genomic Ectromelia virus DNA using PCR techniques and synthesized oligonucleotide primers. The primers added a Not 1 site at the 5' end and the motif Gly-Ser-6xHIS at the 3' end for use in purification processes. After the Gly-Ser-6xHIS motif the primers added an in-frame termination codon and a Bgl 2 site. The PCR product was cut and cloned in pDC409 expression vector (McMahon et al., *EMBO J.* 10: 2821,1991).

The resulting DNA construct was transiently transfected into the monkey cell line COS-1 (ATCC CRL-1650). Following a 7 day culture in medium containing 0.5% low immunoglobulin bovine serum, cell supernatants were harvested and a solution of 0.2% sodium azide was added to the supernatants. The supernatants were filtered through a 0.22 µm filter, concentrated 10 fold with a prep scale concentrator (Millipore; Bedford, Mass.) and purified on a BioCad HPLC protein purification equipped with a Nickel NTA Superflow self pack resin column (Qiagen, Santa Clarita, Calif.). After the supernatant passed through the column, the column was washed with Buffer A (2 mM NaPO4, pH7.4; 300mMNaCl; 50 mM Imidazole). Bound protein was then eluted from the column using a gradient elution techniques. Fractions containing protein were collected and analyzed on a 4–20% SDS-PAGE reducing gel. Peaks containing A39R/polyHis fusion protein were pooled, concentrated 2 fold, and then dialyzed in PBS. The resulting A39R/polyHIS fusion protein was then filtered through a 0.22 µm sterile filter.

EXAMPLE 3

Screening Cell Lines for Binding to A39R

The A39R/Fc fusion protein prepared as described in Example 1 was used to screen cell lines for binding using quantitative binding studies according to standard flow cytometry methodologies. For each cell line screened, the procedure involved incubating approximately 100,000 of the cells blocked with 2% FCS (fetal calf serum), 5% normal goat serum and 5% rabbit serum in PBS for 1 hour. Then the blocked cells were incubated with 5 µg/mL of A39R/Fc fusion protein in 2% FCS, 5% goat serum and 5% rabbit serum in PBS. Following the incubation the sample was washed 2 times with FACS buffer (2% FCS in PBS) and then treated with mouse anti human Fc/biotin (purchased from Jackson Research) and SAPE (streptavidin-phycoerythrin purchased from Molecular Probes). This treatment causes the antihuman Fc/biotin to bind to any bound A39R/Fc and the SAPE to bind to the anti-human Fc/biotin resulting in a fluorescent identifying label on A39R/Fc which is bound to cells. The cells were analyzed for any bound protein using fluorescent detection flow cytometry. The results indicated the A39R semaphorin binds well to human NK cells, murine splenic B cells, human PB T cells, human T, B, erythroid, lymphoid and myeloid precursor cells, fibroblasts and epithelial lineage. Table I details the results of the flow cytometry studies. A "+" indicates that binding was detected between the cell surface and A39R. A "–" indicates that no binding was detected between the cell surface and A39R.

TABLE I

| Cell Line | | A39R Binding Result |
|---|---|---|
| Namalwa | (B cell-like lymphoma - human) | + |
| CB23 | (Human Cord Blood B Cell Line) | + |
| EU-1 | (Human pre B Cell Line) | + |
| MP-1 | (Human B Cell Lymphoma) | + |
| PB B | (Human Peripheral Blood B Cells) | + |
| Mouse Splenic B Cells | | + |
| Mouse Splenic B Cells + CD40L | | + |
| U937 | (Human Monocyte-Type Cell) | + |
| HSB2 | (Human T Cell Line) | + |
| K299 | (Non Hodgkin's Lymphoma) | + |
| TE71 | (Mouse Thymic Epithelium) | + |
| IEC18 | (Rat Intestinal Epithelium) | + |
| IMTLH | (Human Bone Marrow Derived Stroma) | + |
| W126 | (Human Lung Epithelium) | + |
| PL-1 | (Human T-Cell Clone) | + |
| VK-1 | Human T-Cell Clone | + |
| Primary Peripheral Blood T Cells | | + |
| Primary Human NK Cells | | + |
| RAJI | (Burkitt's Lymphoma) | – |
| KG1 | (Human myeloid Cell Line) | – |
| THP-1 | (Human Promonocytic Cell Line) | + |
| MC6 | (Mouse Mast Cell) | – |
| EL4 | (Mouse Thymoma) | – |
| BeWo | (Chorio Carcinoma) | – |
| Primary Mouse Dendritic Cells | | + |
| Primary Human Dendritic Cells | | + |

EXAMPLE 4

Identifying A Putative Semaphorin Receptor

CB23 cells (human cord blood B cell line) and human PB T cells that tested positive for binding to A39R were tested for expression of a putative receptor and to determine if any receptor is expressed as a membrane bound molecule, soluble molecule, or both. Broadly, the analyses involved radiolabeling CB23 and human PB T cell surfaces, harvesting and treating cell supernatants and lysates with an A39RIFc fusion protein to precipitate any putative receptor, and then visualizing an immunoprecipitate on an electrophoretic gel.

In particular, the procedure involved first radiolabeling approximately 1×10⁷ CB23 or PB T cells with [$^{125}$I] as described by Benjamin et al.; Blood 75,:2017–2023 (1990). Cultured cell supernatants were harvested and clarified by centrifugation at 14,000 rpm for 30 minutes. Cell lysates were generated by incubating the cells on ice for 30 minutes in 1 mm L phosphate-buffered saline with 1% Triton-X 100 containing protease inhibitors phenylmethylsulfonyl fluoride, Pepstatin-A, and Leupeptin. The lysates were clarified by centrifugation at 14,000 rpm for 30 minutes. In order to precipitate any receptor present in the lysate and/or supernatant, 200 μL of the cell supernatant or lysate was incubated with 2 μg of A39R/Fc fusion protein prepared as described in Example 1. The incubation was carried out for 1 hour with gentle rocking at 4° C. An Fc protein control sample was prepared and incubation in the same manner. Following the incubation, Protein-A Sepharose beads (#17-0780-01 Pharmacia Biotech Inc., Piscataway, N.J.) were added to the lysates and supernatants and the mixture was incubated for 1 hour with gentle rocking at 4° C. The beads were washed extensively with a PBS 1% Triton-X 100 solution. Bound protein was eluted and analyzed by SDS PAGE. Protein bands were visualized by autoradiography and a single, approximately 200 K Da band was found to bind to A39R/Fc but not to the control Fc Protein. The semaphorin receptor was present in cell lysate and cell supernatant, confirming its expression as membrane bound protein and as a secreted soluble protein.

EXAMPLE 5

Isolating and Sequencing a Semaphorin Receptor

The A39R/Fc fusion protein, prepared as described in Example 1, was used to isolate a human semaphorin receptor polypeptide and a procedure for the isolated polypeptide purification was confirmed. The semaphorin receptor was isolated by suspending CB23 cell pellets in a solution of protease inhibitors that included 1 mM each of PMSF, Leupeptin, Aprotinin, Pepstatin A, 10 μg/mL APMSF, and 1 mM EDTA in homogenization buffer (10 mM phosphate, 30 mM NaCl, pH 7.4). The cells were dounce homogenized and layered over a solution of 41% sucrose in homogenization buffer and the spun down in a Beckman SW-28 rotor at 25,000 rpm, at 4° C. for 45 minutes. The interphases were collected and diluted in cold homogenization buffer, dounced, and spun. The resulting clean membrane pellets were stored at −80 ° C.

Membrane pellets prepared from 240 mLs of packed cells were combined with 100 mLs of an aqueous solution of 20 mM Tris, 150 mM NaCl, the protease inhibitors identified above, 1% Triton X-100 and 0.1 mM of $CaCl_2$, $MgCl_2$, and $McCl_2$ salts (Buffer A). The suspended pellets were dounced and spun in a SW-28 rotor for 30 minutes at 25,000 rpm at 4° C. The supernatant was placed onto a 100 mL wheat germ agglutinin column and allowed to elute at a rate of 1 mL/minute with 10 column volumes of Buffer A. Proteins that were specifically bound to the column were then eluted with Buffer A containing 0.2 M N-acetyl glucosamine.

Fractions testing positive for protein were pooled and incubated with 100 μg of A39R/Fc fusion protein for 1 hour at 4° C. The incubated mixture was run through a sepharose column to remove material that did not specifically bind and then allowed to pass through a 0.5 mL column of Protein A/Sepharose solid support. The Protein A/Sepharose solid support was washed with 20 column volumes of PBS containing 1% Triton X-100 followed by a wash with PBS to wash off any unbound material. Then proteins that were retained on the Protein A/Sepharose column were eluted in a stepwise manner with 0.35 mL fractions of 50 mM citrate at pH 3.0. Fractions that tested positive for protein were combined and concentrated to 50 μL using a 10 kD MWCO Centricon concentrator. Protein in the resulting concentrated sample were reduced and then alkylated using standard DTT and iodoacetic acid procedures. The alkylation proteins were then electrophoresed on an 8% gel. Proteins on the gel were visualized with coomassie-G in 50% MeOH containing 5% acetic acid and then destained in 50% MeOH.

The approximately 200 kD band, located by comparison to protein standards, was excised with a razor blade and washed overnight in 100 mM ammonium carbonate. The gel slice was speed evaporated until dry and a 1:10 solution of trypsin in 100 mM ammonium carbonate was added to the dried slide. The slide was incubated at 37° C. for 16 hours and then protein in the slice was extracted with 50% acetonitrile with 5% formic acid three times while incubating 30 minutes with each extraction.

The trypsin digested peptide fragments were lyophilized, reconstituted in 50 μL of 0.1% trifluoroacetic acid, and separated by RP-HPLC on a 500 μ L id x 25 cm capillary column packed with C-18 reverse phase packing. The HPLC liquid phase was an acetonitrile/water gradient of 10% after 5 minutes, 85% after 105 minutes. Eluting protein was detected at 215 nm. Each protein was collected as it eluted in separate fractions and N-terrninal sequence analysis of the peptides in the fraction was performed on a 494 Procise sequencer according to the manufacturer's instruction.

RP-HPLC fractions, obtained as described above, were dried on a vacuum centrifuge and peptides in the fraction were dissolved in 6 μL of 50% methanol containing 0.5% acetic acid. Two microliters (2 μL) of each of the peptide solutions were loaded into nanospray tips (Protein Analysis Company, Odense, Denmark). Data were obtained with a Finnigan TSQ700 triple quadrupole mass spectrometer (San Jose, Calif.) equipped with a nanospray source. Mass spectra were acquired at unit resolution. For tandem mass spectrometry, the first quadrupole was operated at a resolution sufficient to pass a 3–4 Da wide window, and the third quadrupole was operated at unit resolution. Collision gas was supplied at a pressure of 4 mTorT. Methyl esterification was performed using standard esterification procedures.

The tandem mass spectrometry analysis of the trypsin generated peptides provided amino acid sequence information for isolated portions of the purified protein. The tandem mass spectral data were used in computer assisted screening of non-redundant protein databases and EST databases using the local SEQUEST algorithm search tool (Eng, J.K et al. J am Soc. Mass 1994). The peptide query sequences GluGluThrProValPheTyrLys corresponding to amino acids 421–428 of SEQ ID NO:2, and AsnIleTyrIleTyrLeuThrAlaGlyLys, corresponding to amino acids 436–445 identified EST No. 248534 (Accession N78220) as containing peptide sequences having 100% identity to the query peptide sequences. The peptide query sequence ThrValLeuPheLeuGlyThrGlyAspGlyGlnleuLeuLys corresponding to amino acids 388–401 identified EST No. R08946 as containing a 100% identity to the query.

The 100% identity between portions of EST 248534 and three peptide fragments of the purified protein strongly suggested that the cDNA contained within EST 248534 represented a portion of the nucleotide sequence for the coding region of the purified protein. A source of semaphorin receptor cDNA was identified using phage library screening methods and PCR primers based upon EST 248534.

The oligonucleotide primers had the following nucleotide sequences:
ATCGCATCAT CTACCTTCAT CCATTCCGAC CTG (SEQ ID NO:9)
TAAACACTCC GAACAGGATT TATGTTTATT GCA (SEQ ID NO:10)

PCR isolation and amplification methodologies were carried out using a panel of human tissue cDNA phage libraries as templates for the PCR reactions. The PCR reaction mixture included 1 µL of phage library stock, PCR oligonucleotide primers at 0.3 µM final concentration, 1×PC2 buffer (Ab Peptides, Inc., St. Louis, Mo.), 0.2 mM each of dATP, dCTP, dGTP, dTTP (Pharmacia Biotech) 0.2 µL of a 16:1 mix Klen-Taq/Vent polymerase (Klen-Taq polymerase, Ab Peptides, Inc. and Vent polymerase, New England Biolabs, Beverly, Mass.) in a 30 µL final reaction volume. The PCR reaction cycles included one cycle at 98° C. for 5 minutes; thirty cycles at 98° C. for 45 seconds, thirty cycles at 68° C. for 45 seconds; thirty cycles at 72° C. for 45 seconds, and 1 cycle at 72° C. for 5 minutes using a Robocycler 96 from Stratagene, La Jolla, Calif. cDNAs in several libraries were positively identified as containing DNA encoding the purified VESPR protein based upon the appearance of an appropriate sized DNA band in electrophoresed PCR product.

Two of the phage libraries, human foreskin fibroblast and human dermal fibroblasts, were chosen for additional analysis. Libraries were plated according to established prodedures and probed with a radiolabeled random primer probe derived from a PCR amplification product using EST 248534 as a template. The PCR conditions used to obtained the amplification product were as described above and the probe was generated using Prime-IT II Random Primer Labeling Kit from Stratagene, La Jolla, Calif . Approximately 1×10⁶ cpm/mL of purified probe was used to probe human foreskin phage libraries on nylon membrane filters overnight at 63° C. in a hybridization buffer of 10× Denhardts solution, 50 mM Tris at pH 7.5, 0.9 M NaCl, 0.01% Sodium Pyrophosphate, 1% sodium dodecyl sulfate, and 200 µg/mL denatured, fragmented salmon sperm DNA. After probing, the probed membranes were washed once in 6×SSC, 0.1% SDS for 20 minutes, once in 2×SSC, 0.1% SDS for 20 minutes, once in 1×SSC, 0.1% SDS for 20 minutes, and once in 0.1×SSC, 0.1% SDS for 20 minutes at 63° C. The probed and washed filters were exposed to X-omat AR X-ray film (Eastman-Kodak Corp.) overnight. Four overlapping cDNAs were identified. The overlapping cDNAs, together with the sequenced trypsin digest generated protein fragments were used to complete and confirm the coding sequence of VESPR as shown in SEQ ID NO: 1 and the amino acid sequence presented in SEQ ID NO:2.

EXAMPLE 6

Monoclonal Antibodies to A39R Semaphorin

This example illustrates a method for preparing antibodies to A39R semaphorin. Purified A39R/Fc was prepared as described in Example 1 above. The purified protein was used to generate antibodies against A39R semaphorin as described in U.S. Pat. No. 4,411,993. Briefly, mice were immunized at 0, 2 and 6 weeks with 10 µg with A39R/Fc. The primary immunization was prepared with TITERMAX adjuvant, from Vaxcell, Inc., and subsequent immunizations were prepared with incomplete Freund's adjuvant (IFA). At 11 weeks, the mice were IV boosted with 3–4 µg A39R/Fc in PBS. Three days after the IV boost, splenocytes were harvested and fused with an Ag8.653 myeloma fusion partner using 50% aqueous PEG 1500 solution. Hybridoma supernatants were screened for A39R antibodies by dot blot assay against A39R/FC and an irrelevant Fc protein.

EXAMPLE 7

Northern Blot Analyses for Tissue Expressing Semaphorin Receptor

The following describes Northern Blot experiments carried out to identify tissue and cell types that express VESPR polypeptides of the present invention. The results confirm the cell binding results obtained using flow cytometry analysis and the A39R/Fc fusion protein.

As described in Example 5, EST data base searches resulted in the discovery of an EST that was believed to be a partial clone of the VESPR of SEQ ID NO:2 (EST 248534). A riboprobe template was generated using PCR techniques and oligonucleotide primers that were based on nucleotides 1–372 of EST 248534. The upstream and down stream primers that encompasses nucleotides 1–372 of EST 248534 had the following sequences:

GCGGGACTCA GAGTCACC (SEQ ID NO:5)

GGATCCTAAT ACGACTCACT ATAGGGAGGA AAC-CACTCCG AAC (SEQ ID NO:6)

The underlined portion is a T7 site.

The two primers were used to isolate and amplify a PCR product from EST248534 for use in generating a riboprobe. The riboprobe was generated using Ambion's MAXiscript SP6/T7 kit by combining 3µL of RNAse free water, 2 µL 10× transcription buffer, 1 µL each of 10 mM dATP/dCTP/dGTP, 5µL 5'/3' EST 248534 PCR Product, 5 pL Amersham [β³²P] UTP 10 mCi/mL, 2µL T7 RNA polymerase at room temperature. The combination was microfuged, spun briefly, and incubated at 37° C. for 30 minutes. Then 1µl DNAse was added to the mixture and allowed to react for 15 minutes at 37° C. The reaction product was passed through two column volumes of G-25 packing (Boehringer). One microliter (1µL) of the riboprobe was counted in a scintillation counter for 1 minute to determine cpm/mL Northern blots were generated by fractionating polyadenylated RNA from a variety of cell lines on a 1.2% agarose formaldehyde gel and blotting the RNA onto Hybond Nylon membranes (Amersham, Arlington Heights, Ill.). Standard northern blot generating procedures as described in Maniatis, (*Molecular Cloning: a Laboratory Manual*, Cold Spring Harbor Lab. Press, 1989) were used. Total RNA multiple tissue northern blots were purchased commercially (BioChain Institute, Inc., San Leandro, Calif. Cat #s 021001, 021002, 021003).

The Northern blots were prehybridized in a 50% formamide hybridization solution (30 mL 20×SSC, 2 niL 100× Denhardt's reagent, 1 mL of 10 mg/mL denatured fragmented salmon sperm DNA, 50 mL 100% formamide and 20 mL 10% SDS. The total RNA blots were pre-hybridized at 42° C. for 4 hours and the polyA+ RNA blots were pre-hybridized at 63° C. for 4 hours. The riboprobe was added to clean hybridization solution (same as prehybridization solution) at a count of 106 cpm/mL. The prehybridization solution was removed from the blots and the hybridization solution and riboprobe were added to the blots. The hybridization was allowed to proceed overnight with gentle shaking. The total RNA blots hybridized at 63° C. and the polyA+ RNA blots hybridized at 63° C.

The probed total RNA blots were washed once for 30 minutes in 2×SSC containing 0.05% SDS at 42° C. and once for 30 minutes in 2×SSC containing 0.05% SDS at 55° C.; twice for 30 minutes in 0.1% SSC containing 0.1% SDS at 63° C.; three times for 30 minutes in 0.1xSSC containing 0.1% SDS and then exposed to X-ray film. The poly A+ blots were washed once for 30 minutes in a 2×SSC solution containing 0.05% SDS at 63° C. and once for 30 minutes in 1×SSC containing 0.1% SDS and then exposed to x-ray film.

The results of probing the Northern blots and visualizing the resulting x-ray film for positively binding probes confirm that VESPR is expressed in the same cells as those that showed positive binding in flow cytometry experiments.

Hybridizing RNA was detected in MP-1, HFF and CB23 cells. Primary tissues showing positive RNA included heart, brain, lung, spleen and placenta. No RNA was detecting in RAJ1 cells.

EXAMPLE 8

Generating AHV Semaphorin Fc Fusion Protein

The following describes preparing an AHV Semaphorin/immunoglobulin fusion protein (AHVSema/Fc). The process included preparing a DNA construct that encodes the fusion protein, transfecting a cell line with the DNA construct, and harvesting supernatants from the transfected cells.

DNA encoding AHV-Sema is described in Ensser et al. *J.Gen. Vir.* 76:1063–1067, 1995. DNA encoding AHV-Sema amino acids 70–653 was isolated and amplified from Alcelaphine herpesvirus DNA strain WC11 (Plowright, W. et al. *Nature* 188:1167–1169, 1960) using PCR techniques and synthesized oligonucleotide primers whose sequences were based on the published AHV-Sema sequence. The upstream oligonucleotide primer introduced a Spe I site. A downstream oligonucleotide primer introduced a Not 1 site downstream of the termination codon. The general method used to isolate the soluble AHVSema is described in Spriggs et al., *J. Virology,* 70:5557 (1996).

A restriction fragment containing a mutein human Fc region of immunoglobulin as described by Goodwin et al. *Cell* 73, 447–456, 1993 was ligated into an expression vector (pDC409) containing a murine IL-7 signal peptide and a FLAG™ octapeptide as described in U.S. Pat. No. 5,011,912. The PCR amplified AHVSema DNA encoding was then ligated into the expression vector containing the mutein human Fc region, the murine IL-7 signal peptide and FLAG™ peptide, in a two way ligation. The resulting DNA construct was transfected into the monkey kidney cell lines CV-1/EBNA (with co-transfection of pSV3neo). After 7 days of culture in medium containing 0.5% low immunoglobulin bovine serum, a solution of 0.2% azide was added to the supernatant and the supernatant was filtered through a 0.22 $\mu$m filter. Then approximately 1 L of culture supernatant was passed through a BioCad Protein A HPLC protein purification system using a 4.6×100 mm Protein A column (POROS 20A from PerSeptive Biosystems) at 10 mL/min. The Protein A column binds the Fc Portion of the fusion protein in the supernatant, immobilizing the fusion protein and allowing other components of the supernatant to pass through the column. The column was washed with 30 mL of PBS solution and bound fusion protein was eluted from the HPLC column with citric acid adjusted to pH 3.0. Eluted purified fusions protein was neutralized as it eluted using 1M HEPES solution at pH 7.4.

EXAMPLE 9

Expressing Recombinant Semaphorin Receptor

Using the semaphorin receptor (VESPR) amino acid sequence of the protein purified as described in Example 5, and information derived from EST database searches and cDNAs obtained using hybridization methodologies with radiolabeled probes, also as described in Example 5, cDNA is generated and cells are transfected with the cDNA to allow expression of recombinant VESPR polypeptide.

The cDNA in DC409 expression vector, derived from pDC406, is transfected in CV1/EBNA cells using standard techniques (McMahan et al., *EMBO J.* 10:2821,1991) More particularly, CVI EBNA cells are plated at a density of $2\times10^6$ cells per 10 cm dish in 10 mL of Dulbeccos Minimum Essential Medium (medium) supplemented with 10% fetal calf serum. The cells are allowed to adhere overnight at 37° C. The medium is replaced with 1.5 mL of medium containing 66.7 $\mu$M chloroquine and a DNA mixture containing 5 $\mu$g of cDNA encoding VESPR. Medium containing 175 $\mu$L and 25 $\mu$L of DEAE dextran is added to the cells. The cells and cDNA are incubated at 37° C. for 5 hours. The cDNA mixture is removed and cells are shocked with 1 mL of fresh medium containing 10% DMSO for 2.5 min. The medium is replaced with fresh medium and the cells are grown for at least 3 days.

To recover soluble forms of VESPR, supernatants containing the soluble form are collected and the VESPR protein recovered using HPLC techniques or affinity chromatography techniques. To recover forms of VESPR that are membrane bound, the transfected cells are harvested, fixed in 1% paraformaldehyde, washed and used in their intact form.

EXAMPLE 10

VESPR Binding Studies

In order to examine the binding characteristics of a receptor polypeptide of the present invention, binding studies were performed by subjecting cells expressing membrane bound VESPR extracellular domain to the slide binding assay described in Goodwin et al. *Cell* 73:447456, (1993) and Spriggs et al., *J Virol* 70:5557 (1996).

The pDC409 expression vector, derived from pDC406 (McMahon et al., *EMBO J.* 10:2821, 1991) but having a single Bgl 2 was selected for the cloning process. VESPR cDNA, encoding amino acids 19–1100, was subcloned into a pDC409 expression vector through the Sal 1 (5') and Not 1 (3') sites, to form a DNA construct.

CV-1/EBNA cells were transfected via DEAE/Dextran with 2 $\mu$g of a VESPR cDNA (encoding amino acids 19–1100) in pDC409 (Giri et al., *EMBO J* 13:2822, 1994). The transfected cells were cultured for 3 days and the CV-1/EBNA cell monolayers were incubated with 1 $\mu$g/inL of A39R/Fc, AHVSema/Fc, or control Fc protein. Then the incubated cells were washed and incubated with $^{125}$I-labeled mouse anti-human IgG (Jackson Immunoresearch, West Grove, Pa.). After extensive washing, the cells were fixed, dipped in photographic emulsion as described by Gearing et al., *EMBO J* 8:3667–3676 (1989) and developed. Positive binding was determined by the presence of exposed or darkened silver grains overlaying cells expressing VESPR that had bound Fc protein.

EXAMPLE 11

Flow Cytometry and Inhibition Binding Studies

The following describes flow cytometric analyses of CB23 cells for binding to A39R/Fc fusion protein (Example 1) and the AHVsema/Fc fusion protein (Example9). Also described below is a study directed to determining inhibition of the AHVsema and A39R binding with and an excess of A39R/polyHis fusion protein prepared as described in Example 2.

The flow cytometric analysis was performed by first incubating about $1x10^6$ CB23 cells on ice for 30 minutes in FACS buffer and containing 3% normal goat serum and 3% normal rabbit serum to block non-specific binding. Portions of A39R/Fc, AHVsema/Fc and a control Fc protein were added at varying concentrations and the incubation was continued for 30 minutes. The cells were washed and then incubated with phycoerythrin-conjugated Fc specific anti-human IgG in FACS buffer. The cells were washed and analyzed on a FACScan from Becton Dickinson, Bedford, Mass. The results showed positive binding of AHV semaphorin and the A39R semaphorin.

Binding inhibition studies were performed by incubating about $1 \times 10^6$ CB23 cells for 30 minutes on ice in FACS buffer. The A39R/polyHis and control HIS protein were added to different samples at varying concentrations and the incubation continued for another 30 minutes. Then A39R/Fc or AHVsema/Fc were added to the incubated cells at varying concentrations and the incubation was continued for another 30 minutes. The cells were washed and then incubated with phycoerythrin-conjugated Fc specific anti-human IgG in FACS buffers. The cells were washed again and then analyzed on a FACScan. The results demonstrated complete inhibition of A39R and AHVSema using A39R/polyHIS, but not the heterologous HIS containing protein.

EXAMPLE 12

Human B Cell Aggregation with A39R Semaphorin

In order to examine human B cell response to A39R semaphorin, human tonsillar B cells were purified as described in Spriggs et al., *J Exp Med* 176:1543, (1992). An A39R/polyHis fusion protein was prepared as described in Example 2. A solution of A39R/polyHis fusion protein was prepared to a final A39R concentration of 1 µg/mL and the A39R/polyHis fusion protein solution was incubated in in vitro cultures of about $10^5$ of the purified B cells. Continuing the incubation for about 24 hours resulted in cellular aggregation. When a 10 fold molar excess of the monoclonal antibody against A39R, prepared as described in Example 6, was added to the fusion protein preparation prior to adding the fusion protein to the cultures, the cell aggregation was blocked. Additionally, when the A39R semaphorin was heat inactivated prior to adding it to the culture, the aggregation was blocked.

This work confirms that VESPR is expressed on B cells and that the interaction between A39R and VESPR results in B cell aggregation. B cell aggregation is indicative of their activation. Activated B cells are known to secrete cytokines, produce antibodies, or become antigen presenting cells.

EXAMPLE 13

Mouse Dendritic Cells and Macrophage Aggregation with A39R Semaphorin

In order to examine dendritic cell and macrophage response to A39R, mouse cell cultures were brought into contact with A39R semaphorin and the effects of the combination noted. Mouse dendritic cell cultures containing macrophages were obtained by immunizing mice with Flt3-L and cells were isolated and purified as described in Maraskovsky et al., *J Exp Med* 184:1953, (1996).

Briefly, female C57B1/6 mice were injected once daily with a solution of 10 µg of Flt3L and 1 µg mouse serum albumin in 100 µL of PBS for 9–10 consecutive days. After the immunization, single cell suspensions of spleens were prepared by disrupting spleen tissue between frosted glass slides in the presence of $NH_2Cl$ to deplete red blood cells. The remaining cells were incubated with mAb to Thy-1, B220, NK1.1, and TER1 19, and then incubated with 10% rabbit complement. Then the incubated cells were washed and residual mAb-coated cells were removed using anti-immunoglobulin (Ig)-coated magnetic beads. The remaining enriched cells were cultured or sorted for the various cell populations.

Cells selected for sorting were stained with anti-CD11c and anti-CD11b and sorted for the C and D/E populations as described in Maraskovsky et al., *J Exp Med* 184:1953–1962, 1996.

An A39R/polylis fusion protein was prepared as described in Example 2. An A39R/polyHis fusion protein solution was incubated in in vitro cultures at a final concentration of 1 µg/mL with about $10^5$ of the sorted or depleted mouse cells. Within 4–6 hours the cells began to aggregate. When a 10 fold molar excess of the monoclonal antibody against A39R, prepared as described in Example 6, was added to the A39R/polyHis fusion protein preparation prior to adding the fusion protein to the mouse cell cultures, the aggregation was blocked.

This work confirms that VESPR is expressed on dendritic cells and macrophages, and that the interaction between A39R and VESPR results in dendritic: cell and macrophage aggregation.

EXAMPLE 14

A39R Semaphorin Upregulates CD69 Activation Antigen

In order to investigate the effects of A39R semaphorin on cultured dendritic cells, mice were injected each day for 9 days with a Flt3-L preparation. Mouse dendritic cells were harvested and then cultured in medium containing 10% FBS and 20 ng/mL GM-CSF for 5 days.

On day 5, 1 µg/ml of A39R/polyHis fusion protein was added to the culture. On day 6, the cells were stained with diagnostic antibodies. The results of the diagnostic antibody staining experiments showed that CD11c+, CD11b cells (dendritic cells) expressed an increased amount of the CD69 activation antigen, thus demonstrating that the interaction of A39R semaphorin and its receptor upregulate CD69 expression.

When the fusion protein is inactivated with heat, the fusion protein had no effect on the CD69 antigen. Representative changes in mean fluorescence intensity between unstained and stained cells were from approximately 500 channels to 2500 channels. Again, these results demonstrate significant effects of the interactions between A39R semaphorin and its membrane bound receptor on the regulation of the CD69 activation antigen, a transient and early expressed marker for cell activation.

EXAMPLE 15

Evaluating the Effect of A39R in the Production of IL-12

In order to study the role of A39R in the production of IL-12 from mouse spleen cells, mice were immunized with flt3-L and dendritic cells were generated, harvested and purified as described in Example 13.

Approximately $5 \times 10^5$ cells/0.5 mL of purified, unsorted dendritic cells were incubated in modified DMEM media (500 µL at $1 \times 10^6$/mL) in the presence of one more of the following: 20 ng/nL muGM-CSF (Immunex, Seattle, Wash.), 20ng/mL γ-IFN (Genzyme, Boston, Mass.), 10 µg/mL SAC (CalBiochem, La Jolla, Calif.). Each cell preparation was treated additionally with 1 µg/mL of A39R/ polyHis fusion protein alone or in combination with 1 μg/mL or 0.1 μg/mL of muCD40L trimer (Immunex, Seattle, Wash.). Cultures were incubated in humidified 37C, 10% $CO_2$-in-air for 16–18 h. After incubation, the viability of each group of cultured cells was determined and supernatants were collected and assayed for muIL12 (P70) using an ELISA assay kit (Genzyme, Boston, Mass.). MuIL12 levels were calculated by reference to a standard curve constructed with recombinant cytokine.

ELISA testing demonstrated in particular that A39R interacts with its receptor to synergize with interferon and SAC in the production of IL-12 from unsorted mouse dendritic cells. This in vivo IL-12 induction promotes natural killer cell activation and gamma interferon production and contributes to upregulating gamma interferon sensitive cytokines.

EXAMPLE 16

Testing Effects of A39R on Regulation of MHC Class II and CD86 on Monocytes

The following experiment describes upregulation of MHC Class II and CD86 by the interaction of A39R with its membrane bound receptor. Peripheral blood from healthy donors was diluted 1:1 in low endotoxin PBS at pH 7.4 and room temperature. Then 35 mLs of the diluted blood was layered over 15 mLs of Isolymph (Gallard and Schlesinger Industries, Inc; Carle Place, N.Y.) and centrifuged at 2200 rpm for 25 minutes at room temperature. The plasma layers was reserved. The PBMC layer was harvested and washed three times to remove the Isolymph. The washed PBMC's were resuspended in X-Vivo 15 serum free media (BioWhittaker, Walkersville, Md.) and added to T175 flasks. The flasks had been previously coated with 2% Gelatin (Sigma, St. Louis, MO) and pre-treated for 30 minutes with the reserved plasma layer. The PBMC's were allowed to adhere for 90 minutes at 37° C., 5% $CO_2$ and then rinsed three times gently with 10 mL washes of low endotoxin PBS. Adhered monocytes were harvested by incubating the cells in Enzyme Free Dissociation Buffer (Gibco, BRL) and washing the cells multiple times in PBS. Monocytes were centrifuged at 2500 rpm for 5 minutes, counted, and set up in 24 well dishes at $5 \times 10^5$ cells/well in 1 mL. The cultures were 95% pure.

Purified monocytes were cultured for 7–9 days in the presence of 20 μg/mL GM-CSF and 100 ng/mL IL-4 in order to allow cells to differentiate to a more dendritic cell-like phenotype. On day 7–9, cultures were treated with 1 μg/mL A39R/polyHis or a control polyHis containing protein, and the next day cells and supernatants were harvested for analyses.

In flow cytometric experiments for examining monocyte-derived dendritic cell surface markers, cells were stained with conjugated mAbs directed against specific proteins. The staining showed that for a majority of the peripheral blood donors tested, A39R treatment downregulated CD86 and MHC class II expression on these cells. Since CD86 and MHC class II molecules are markers of an enhanced antigen presentation by dendritic cells, their downregulation suggests an immunosuppressive effect of the interaction of A39R with its receptor on this cell population.

EXAMPLE 17

Upregulation of CD54

The following describes the effect of the interaction between A39R semaphorin and its receptor on purified monocytes and more particularly, the impact of CD54 expression on monocytes after incubation with a semaphorin. Freshly isolated monocytes were purified from peripheral blood donors as described in Example 16, except that they were held in culture overnight in the presence of A39R/polyHis or control proteins.

Following the overnight culture, flow cytometry was performed using the cultured cells and mAbs directed against monocyte specific cell surface markers. In all donors tested, the level of CD54 surface expression was enhanced in the presence of A39R, but not in the presence of heat inactivated A39R. Similarly, in cultures containing control proteins CD54 surface expression was not enhanced.

CD54, also known as ICAM-1, is an adhesion molecule whose increased expression is considered to be indicative of cellular activation. These data indicate that promoting the interaction of A39R with its receptor can activate freshly isolated human monocytes.

EXAMPLE 18

Cytokine Induction from Freshly Isolated Human Monocytes

Freshly isolated human monocytes were purified as described in Example 16, and cultured as described in Example 17. After the overnight incubation with A39R/polyHis, monocyte supernatants were examined for the presence of proinflammatory cytokines. In all donors tested, IL-6 and IL-8 was induced by A39R protein. Heat inactivated A39R and control proteins did not inducted IL-6 or IL-8. Additionally, cytokine production was blocked by the inclusion of a mAb directed against A39R.

The results of this experiment demonstrate that A39R, or homologues of this protein, interacting with its receptor, can induce cytokine production by freshly isolated monocytes. Advantageously, soluble forms of VESPR can be used in inhibit the proinflammatory activity of monocytes in response to A39R or its homologues.

EXAMPLE 19

Monocyte Aggregation Studies

In order to examine human monocyte response to the interaction of a semaphorin to its receptor on monocytes, monocytes were purified as described in Example 17 and an A39R/polyHIS fusion protein was prepared as described in Example 2. The fusion protein and purified, cultured monocytes were incubated. Continuing the incubation for 20 hours resulted in monocyte aggregation. In view of the results demonstrated in Example 17, it is suggested that the observed monocyte aggregation occurs as a result of CD54 upregulation. However, other factors may contribute to the aggregation as well.

This work confirms that the semaphorin receptor of the present invention is expressed on monocytes and that the interaction between A39R and VESPR results in monocyte aggregation. Similar to B cells, monocytes aggregation is indicative of their activation.

EXAMPLE 20

Monoclonal Antibodies to VESPR

This example illustrates a method for preparing antibodies to VESPR polypeptides. Purified VESPR polypeptide is prepared as described in Example 10. The purified protein is used to generate antibodies against VESPR as described in U.S. Pat. No. 4,411,993. Briefly, mice are immunized at 0, 2 and 6 weeks with 10 µg with VESPR. The primary immunization is prepared with TITERMAX adjuvant, from Vaxcell, Inc., and subsequent immunizations are prepared with incomplete Freund's adjuvant (IFA). At 11 weeks, the mice are IV boosted with 3–4 µg VESPR in PBS. Three days after the IV boost, splenocytes are harvested and fused with an Ag8.653 myeloma fusion partner using 50% aqueous PEG 1500 solution. Hybridoma supernatants are screened for VESPR antibodies by dot blot assay against VESPR and an irrelevant Fc protein.

What is claimed is:

1. An isolated polypeptide comprising the amino acid sequence of SEQ ID NO:2.

2. An isolated polypeptide comprising an amino acid sequence that is at least 90% identical to the amino acid sequence of SEQ ID NO:2, wherein the percent identity is calculated using the GAP program with a unary comparison matrix, a 3.0 gap penalty, an additional 0.10 penalty for each symbol in each gap, and no penalty for end gaps, and the polypeptide binds a polypeptide selected from the group consisting of A39R semaphorin and AHV semaphorin.

3. An isolated polypeptide encoded by DNA selected from the group consisting of:
   (a) cDNA of SEQ ID NO:1; and
   (b) DNA sequences that hybridize under moderately stringent conditions of 55° C. in 5 X SSC, overnight, to the cDNA of (a); and which DNA sequences encode a polypeptide that binds a polypeptide selected from the group consisting of A39R semaphorin and AHV semaphorin.

4. A soluble polypeptide comprising an amino acid sequence selected from the group consisting of:
   (a) amino acids $x_1$ to 945, inclusive, of SEQ ID NO:2, wherein $x_1$ is amino acid 1 or 35;
   (b) a fragment of the sequence of (a), wherein the fragment binds a polypeptide selected from the group consisting of A39R semaphorin and AHV semaphorin.

5. A soluble polypeptide comprising an amino acid sequence that is at least 90% identical to an amino acid sequence selected from the group consisting of
   (a) amino acids $x_1$ to 945 of SEQ ID NO:2, wherein $x_1$ is amino acid 1 or 35 and,
   (b) a fragment of the sequence of (a);
wherein the percent identity is calculated using the GAP program with a unary comparison matrix, a 3.0 gap penalty, an additional 0.10 penalty for each symbol in each gap, and no penalty for end gaps, and, wherein the soluble polypeptide binds a polypeptide selected from the group consisting of A39R semaphorin and AHV semaphorin.

6. A composition comprising a suitable diluent carrier and a polypeptide of claim 2.

7. The polypeptide of claim 5 comprising the sequence of amino acids 35 to 944 of SEQ ID) NO:2.

8. A soluble polypeptide having the sequence of amino acids 380 to 482 of SEQ ID NO:2 and which binds a polypeptide selected from the group consisting of A39R semaphorin and AHV semaphorin.

9. An isolated polypeptide having the sequenc of amino acids 966 to 1568 of SEQ ID NO:2 and which binds a polypeptide selected from the group consisting of A39R semaphorin and AHV semaphorin.

10. The polypeptide of claim 1 attached to a drug, toxin, radionuclide, chromophore and/or enzyme.

11. The polypeptide of claim 2 attached to a drug, toxin, radionuclide, chromophore and/or enzyme.

12. The polypeptide of claim 3 attached to a drug, toxin, radionuclide, chromophore and/or enzyme.

13. The polypeptide of claim 4 attached to a drug, toxin, radionuclide, chromophore and/or enzyme.

14. The polypeptide of claim 5 attached to a drug, toxin, radionuclide, chromophore and/or enzyme.

15. The composition of claim 6 wherein the polypeptide is attached to a drug, toxin, radionuclide, chromophore and/or enzyme.

16. The polypeptide of claim 7 attached to a drug, toxin, radionuclide, chromophore and/or enzyme.

17. The polypeptide of claim 8 attached to a drug, toxin, radionuclide, chromophore and/or enzyme.

18. The polypeptide of claim 9 attached to a drug, toxin, radionuclide, chromophore and/or enzyme.

19. The polypeptide of claim 1 fused to an Fc region of an antibody.

20. The polypeptide of claim 2 fused to an Fc region of an antibody.

21. The polypeptide of claim 3 fused to an Fc region of an antibody.

22. The polypeptide of claim 4 fused to an Fc region of an antibody.

23. The polypeptide of claim 5 fused to an Fc region of an antibody.

24. The composition of claim 6 wherein the polypeptide is fused to an Fc region of an antibody.

25. The polypeptide of claim 7 fused to an Fc region of an antibody.

26. The polypeptide of claim 8 fused to an Pc region of an antibody.

27. The polypeptide of claim 9 fused to an Fc region of an antibody.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 4707 base pairs
      (B) TYPE: nucleic acid
      (C) STRANDEDNESS: double
      (D) TOPOLOGY: linear (ii) MOLECULE TYPE: cDNA (iii) HYPOTHETICAL: NO (iv) ANTI-SENSE: NO (ix) FEATURE:
      (A) NAME/KEY: CDS
      (B) LOCATION: 1..4707

(xi) SEQUENCE DESCRIPTION: SEQ ID NO:1:

```
ATG GAG GTC TCC CGG AGG AAG GCG CCG CCG CGC CCC CCG CGC CCC GCA       48
Met Glu Val Ser Arg Arg Lys Ala Pro Pro Arg Pro Pro Arg Pro Ala
 1               5                  10                  15

GCG CCA CTG CCC CTG CTC GCC TAT CTG CTG GCA CTG GCG GCT CCC GGC       96
Ala Pro Leu Pro Leu Leu Ala Tyr Leu Leu Ala Leu Ala Ala Pro Gly
             20                  25                  30

CGG GGC GCG GAC GAG CCC GTG TGG CGG TCG GAG CAA GCC ATC GGA GCC      144
Arg Gly Ala Asp Glu Pro Val Trp Arg Ser Glu Gln Ala Ile Gly Ala
         35                  40                  45

ATC GCG GCG AGC CAG GAG GAC GGC GTG TTT GTG GCG AGC GGC AGC TGC      192
Ile Ala Ala Ser Gln Glu Asp Gly Val Phe Val Ala Ser Gly Ser Cys
     50                  55                  60

CTG GAC CAG CTG GAC TAC AGC CTG GAG CAC AGC CTC TCG CGC CTG TAC      240
Leu Asp Gln Leu Asp Tyr Ser Leu Glu His Ser Leu Ser Arg Leu Tyr
 65                  70                  75                  80

CGG GAC CAA GCG GGC AAC TGC ACA GAG CCG GTC TCG CTG GCG CCC CCC      288
Arg Asp Gln Ala Gly Asn Cys Thr Glu Pro Val Ser Leu Ala Pro Pro
                 85                  90                  95

GCG CGG CCC CGG CCC GGG AGC AGC TTC AGC AAG CTG CTG CTG CCC TAC      336
Ala Arg Pro Arg Pro Gly Ser Ser Phe Ser Lys Leu Leu Leu Pro Tyr
            100                 105                 110

CGC GAG GGG GCG GCC GGC CTC GGG GGG CTG CTG CTC ACC GGC TGG ACC      384
Arg Glu Gly Ala Ala Gly Leu Gly Gly Leu Leu Leu Thr Gly Trp Thr
        115                 120                 125

TTC GAC CGG GGC GCC TGC GAG GTG CGG CCC CTG GGC AAC CTG AGC CGC      432
Phe Asp Arg Gly Ala Cys Glu Val Arg Pro Leu Gly Asn Leu Ser Arg
    130                 135                 140

AAC TCC CTG CGC AAC GGC ACC GAG GTG GTG TCG TGC CAC CCG CAG GGC      480
Asn Ser Leu Arg Asn Gly Thr Glu Val Val Ser Cys His Pro Gln Gly
145                 150                 155                 160

TCG ACG GCC GGC GTG GTG TAC CGC GCG GGC CGG AAC AAC CGC TGG TAC      528
Ser Thr Ala Gly Val Val Tyr Arg Ala Gly Arg Asn Asn Arg Trp Tyr
```

```
                       165                 170                 175
CTG GCG GTG GCC GCC ACC TAC GTG CTG CCT GAG CCG GAG ACG GCG AGC        576
Leu Ala Val Ala Ala Thr Tyr Val Leu Pro Glu Pro Glu Thr Ala Ser
            180                 185                 190

CGC TGC AAC CCC GCG GCA TCC GAC CAC GAC ACG GCC ATC GCG CTC AAG        624
Arg Cys Asn Pro Ala Ala Ser Asp His Asp Thr Ala Ile Ala Leu Lys
            195                 200                 205

GAC ACG GAG GGG CGC AGC CTG GCC ACG CAG GAG CTG GGG CGC CTC AAG        672
Asp Thr Glu Gly Arg Ser Leu Ala Thr Gln Glu Leu Gly Arg Leu Lys
            210                 215                 220

CTG TGC GAG GGC GCG GGC AGC CTG CAC TTC GTG GAC GCC TTT CTC TGG        720
Leu Cys Glu Gly Ala Gly Ser Leu His Phe Val Asp Ala Phe Leu Trp
225             230                 235                 240

AAC GGC AGC ATC TAC TTC CCC TAC TAC CCC TAC AAC TAT ACG AGC GGC        768
Asn Gly Ser Ile Tyr Phe Pro Tyr Tyr Pro Tyr Asn Tyr Thr Ser Gly
                245                 250                 255

GCT GCC ACC GGC TGG CCC AGC ATG GCG CGC ATC GCG CAG AGC ACC GAG        816
Ala Ala Thr Gly Trp Pro Ser Met Ala Arg Ile Ala Gln Ser Thr Glu
            260                 265                 270

GTG CTG TTC CAG GGC CAG GCA TCC CTC GAC TGC GGC CAC GGC CAC CCC        864
Val Leu Phe Gln Gly Gln Ala Ser Leu Asp Cys Gly His Gly His Pro
            275                 280                 285

GAC GGC CGC CGC CTG CTC CTC TCC TCC AGC CTA GTG GAG GCC CTG GAC        912
Asp Gly Arg Arg Leu Leu Leu Ser Ser Ser Leu Val Glu Ala Leu Asp
290             295                 300

GTC TGG GCG GGA GTG TTC AGC GCG GCC GCT GGA GAG GGC CAG GAG CGG        960
Val Trp Ala Gly Val Phe Ser Ala Ala Ala Gly Glu Gly Gln Glu Arg
305             310                 315                 320

CGC TCC CCC ACC ACC ACG GCG CTC TGC CTC TTC AGA ATG AGT GAG ATC       1008
Arg Ser Pro Thr Thr Thr Ala Leu Cys Leu Phe Arg Met Ser Glu Ile
                325                 330                 335

CAG GCG CGC GCC AAG AGG GTC AGC TGG GAC TTC AAG ACG GCC GAG AGC       1056
Gln Ala Arg Ala Lys Arg Val Ser Trp Asp Phe Lys Thr Ala Glu Ser
            340                 345                 350

CAC TGC AAA GAA GGG GAT CAA CCT GAA AGA GTC CAA CCA ATC GCA TCA       1104
His Cys Lys Glu Gly Asp Gln Pro Glu Arg Val Gln Pro Ile Ala Ser
            355                 360                 365

TCT ACC TTG ATC CAT TCC GAC CTG ACA TCC GTT TAT GGC ACC GTG GTA       1152
Ser Thr Leu Ile His Ser Asp Leu Thr Ser Val Tyr Gly Thr Val Val
    370                 375                 380

ATG AAC AGG ACT GTT TTA TTC TTG GGG ACT GGA GAT GGC CAG TTA CTT       1200
Met Asn Arg Thr Val Leu Phe Leu Gly Thr Gly Asp Gly Gln Leu Leu
385             390                 395                 400

AAG GTT ATT CTT GGT GAG AAT TTG ACT TCA AAT TGT CCA GAG GTT ATC       1248
Lys Val Ile Leu Gly Glu Asn Leu Thr Ser Asn Cys Pro Glu Val Ile
                405                 410                 415

TAT GAA ATT AAA GAA GAG ACA CCT GTT TTC TAC AAA CTC GTT CCT GAT       1296
Tyr Glu Ile Lys Glu Glu Thr Pro Val Phe Tyr Lys Leu Val Pro Asp
            420                 425                 430

CCT GTG AAG AAT ATC TAC ATT TAT CTA ACA GCT GGG AAA GAG GTG AGG       1344
Pro Val Lys Asn Ile Tyr Ile Tyr Leu Thr Ala Gly Lys Glu Val Arg
            435                 440                 445

AGA ATT CGT GTT GCA AAC TGC AAT AAA CAT AAA TCC TGT TCG GAG TGT       1392
Arg Ile Arg Val Ala Asn Cys Asn Lys His Lys Ser Cys Ser Glu Cys
450             455                 460

TTA ACA GCC ACA GAC CCT CAC TGC GGT TGG TGC CAT TCG CTA CAA AGG       1440
Leu Thr Ala Thr Asp Pro His Cys Gly Trp Cys His Ser Leu Gln Arg
465             470                 475                 480

TGC ACT TTT CAA GGA GAT TGT GTA CAT TCA GAG AAC TTA GAA AAC TGG       1488
```

```
                Cys Thr Phe Gln Gly Asp Cys Val His Ser Glu Asn Leu Glu Asn Trp
                                485                 490                 495

CTG GAT ATT TCG TCT GGA GCA AAA AAG TGC CCT AAA ATT CAG ATA ATT                    1536
Leu Asp Ile Ser Ser Gly Ala Lys Lys Cys Pro Lys Ile Gln Ile Ile
            500                 505                 510

CGA AGC AGT AAA GAA AAG ACT ACA GTG ACT ATG GTG GGA AGC TTC TCT                    1584
Arg Ser Ser Lys Glu Lys Thr Thr Val Thr Met Val Gly Ser Phe Ser
            515                 520                 525

CCA AGA CAC TCA AAG TGC ATG GTG AAG AAT GTG GAC TCT AGC AGG GAG                    1632
Pro Arg His Ser Lys Cys Met Val Lys Asn Val Asp Ser Ser Arg Glu
        530                 535                 540

CTC TGC CAG AAT AAA AGT CAG CCC AAC CGG ACC TGC ACC TGT AGC ATC                    1680
Leu Cys Gln Asn Lys Ser Gln Pro Asn Arg Thr Cys Thr Cys Ser Ile
545                 550                 555                 560

CCA ACC AGA GCA ACC TAC AAA GAT GTT TCA GTT GTC AAC GTG ATG TTC                    1728
Pro Thr Arg Ala Thr Tyr Lys Asp Val Ser Val Val Asn Val Met Phe
                565                 570                 575

TCC TTC GGT TCT TGG AAT TTA TCA GAC AGA TTC AAC TTT ACC AAC TGC                    1776
Ser Phe Gly Ser Trp Asn Leu Ser Asp Arg Phe Asn Phe Thr Asn Cys
            580                 585                 590

TCA TCA TTA AAA GAA TGC CCA GCA TGC GTA GAA ACT GGC TGC GCG TGG                    1824
Ser Ser Leu Lys Glu Cys Pro Ala Cys Val Glu Thr Gly Cys Ala Trp
            595                 600                 605

TGT AAA AGT GCA AGA AGG TGT ATC CAC CCC TTC ACA GCT TGC GAC CCT                    1872
Cys Lys Ser Ala Arg Arg Cys Ile His Pro Phe Thr Ala Cys Asp Pro
        610                 615                 620

TCT GAT TAT GAG AGA AAC CAG GAA CAG TGT CCA GTG GCT GTC GAG AAG                    1920
Ser Asp Tyr Glu Arg Asn Gln Glu Gln Cys Pro Val Ala Val Glu Lys
625                 630                 635                 640

ACA TCA GGA GGA GGA AGA CCC AAG GAG AAC AAG GGG AAC AGA ACC AAC                    1968
Thr Ser Gly Gly Gly Arg Pro Lys Glu Asn Lys Gly Asn Arg Thr Asn
                645                 650                 655

CAG GCT TTA CAG GTC TTC TAC ATT AAG TCC ATT GAG CCA CAG AAA GTA                    2016
Gln Ala Leu Gln Val Phe Tyr Ile Lys Ser Ile Glu Pro Gln Lys Val
            660                 665                 670

TCG ACA TTA GGG AAA AGC AAC GTG ATA GTA ACG GGA GCA AAC TTT ACC                    2064
Ser Thr Leu Gly Lys Ser Asn Val Ile Val Thr Gly Ala Asn Phe Thr
            675                 680                 685

CGG GCA TCG AAC ATC ACA ATG ATC CTG AAA GGA ACC AGT ACC TGT GAT                    2112
Arg Ala Ser Asn Ile Thr Met Ile Leu Lys Gly Thr Ser Thr Cys Asp
        690                 695                 700

AAG GAT GTG ATA CAG GTT AGC CAT GTG CTA AAT GAC ACC CAC ATG AAA                    2160
Lys Asp Val Ile Gln Val Ser His Val Leu Asn Asp Thr His Met Lys
705                 710                 715                 720

TTC TCT CTT CCA TCA AGC CGG AAA GAA ATG AAG GAT GTG TGT ATC CAG                    2208
Phe Ser Leu Pro Ser Ser Arg Lys Glu Met Lys Asp Val Cys Ile Gln
                725                 730                 735

TTT GAT GGT GGG AAC TGC TCT TCT GTG GGA TCC TTA TCC TAC ATT GCT                    2256
Phe Asp Gly Gly Asn Cys Ser Ser Val Gly Ser Leu Ser Tyr Ile Ala
            740                 745                 750

CTG CCA CAT TGT TCC CTT ATA TTT CCT GCT ACC ACC TGG ATC AGT GGT                    2304
Leu Pro His Cys Ser Leu Ile Phe Pro Ala Thr Thr Trp Ile Ser Gly
            755                 760                 765

GGT CAA AAT ATA ACC ATG ATG GGC AGA AAT TTT GAT GTA ATT GAC AAC                    2352
Gly Gln Asn Ile Thr Met Met Gly Arg Asn Phe Asp Val Ile Asp Asn
        770                 775                 780

TTA ATC ATT TCA CAT GAA TTA AAA GGA AAC ATA AAT GTC TCT GAA TAT                    2400
Leu Ile Ile Ser His Glu Leu Lys Gly Asn Ile Asn Val Ser Glu Tyr
785                 790                 795                 800
```

```
                                                      -continued

TGT GTG GCG ACT TAC TGC GGG TTT TTA GCC CCC AGT TTA AAG AGT TCA    2448
Cys Val Ala Thr Tyr Cys Gly Phe Leu Ala Pro Ser Leu Lys Ser Ser
            805                 810                 815

AAA GTG CGC ACG AAT GTC ACT GTG AAG CTG AGA GTA CAA GAC ACC TAC    2496
Lys Val Arg Thr Asn Val Thr Val Lys Leu Arg Val Gln Asp Thr Tyr
        820                 825                 830

TTG GAT TGT GGA ACC CTG CAG TAT CGG GAG GAC CCC AGA TTC ACG GGG    2544
Leu Asp Cys Gly Thr Leu Gln Tyr Arg Glu Asp Pro Arg Phe Thr Gly
        835                 840                 845

TAT CGG GTG GAA TCC GAG GTG GAC ACA GAA CTG GAA GTG AAA ATT CAA    2592
Tyr Arg Val Glu Ser Glu Val Asp Thr Glu Leu Glu Val Lys Ile Gln
850                 855                 860

AAA GAA AAT GAC AAC TTC AAT ATT TCC AAA AAA GAC ATT GAA ATT ACT    2640
Lys Glu Asn Asp Asn Phe Asn Ile Ser Lys Lys Asp Ile Glu Ile Thr
865                 870                 875                 880

CTC TTC CAT GGG GAA AAT GGG CAA TTA AAT TGC AGT TTT GAA AAT ATT    2688
Leu Phe His Gly Glu Asn Gly Gln Leu Asn Cys Ser Phe Glu Asn Ile
            885                 890                 895

ACT AGA AAT CAA GAT CTT ACC ACC ATC CTT TGC AAA ATT AAA GGC ATC    2736
Thr Arg Asn Gln Asp Leu Thr Thr Ile Leu Cys Lys Ile Lys Gly Ile
        900                 905                 910

AAG ACT GCA AGC ACC ATT GCC AAC TCT TCT AAG AAA GTT CGG GTC AAG    2784
Lys Thr Ala Ser Thr Ile Ala Asn Ser Ser Lys Lys Val Arg Val Lys
        915                 920                 925

CTG GGA AAC CTG GAG CTC TAC GTC GAG CAG GAG TCA GTT CCT TCC ACA    2832
Leu Gly Asn Leu Glu Leu Tyr Val Glu Gln Glu Ser Val Pro Ser Thr
930                 935                 940

TGG TAT TTT CTG ATT GTG CTC CCT GTC TTG CTA GTG ATT GTC ATT TTT    2880
Trp Tyr Phe Leu Ile Val Leu Pro Val Leu Leu Val Ile Val Ile Phe
945                 950                 955                 960

GCG GCC GTG GGG GTG ACC AGG CAC AAA TCG AAG GAG CTG AGT CGC AAA    2928
Ala Ala Val Gly Val Thr Arg His Lys Ser Lys Glu Leu Ser Arg Lys
            965                 970                 975

CAG AGT CAA CAA CTA GAA TTG CTG GAA AGC GAG CTC CGG AAA GAG ATA    2976
Gln Ser Gln Gln Leu Glu Leu Leu Glu Ser Glu Leu Arg Lys Glu Ile
        980                 985                 990

CGT GAC GGC TTT GCT GAG CTG CAG ATG GAT AAA TTG GAT GTG GTT GAT    3024
Arg Asp Gly Phe Ala Glu Leu Gln Met Asp Lys Leu Asp Val Val Asp
        995                 1000                1005

AGT TTT GGA ACT GTT CCC TTC CTT GAC TAC AAA CAT TTT GCT CTG AGA    3072
Ser Phe Gly Thr Val Pro Phe Leu Asp Tyr Lys His Phe Ala Leu Arg
        1010                1015                1020

ACT TTC TTC CCT GAG TCA GGT GGC TTC ACC CAC ATC TTC ACT GAA GAT    3120
Thr Phe Phe Pro Glu Ser Gly Gly Phe Thr His Ile Phe Thr Glu Asp
1025                1030                1035                1040

ATG CAT AAC AGA GAC GCC AAC GAC AAG AAT GAA AGT CTC ACA GCT TTG    3168
Met His Asn Arg Asp Ala Asn Asp Lys Asn Glu Ser Leu Thr Ala Leu
            1045                1050                1055

GAT GCC CTA ATC TGT AAT AAA AGC TTT CTT GTT ACT GTC ATC CAC ACC    3216
Asp Ala Leu Ile Cys Asn Lys Ser Phe Leu Val Thr Val Ile His Thr
        1060                1065                1070

CTT GAA AAG CAG AAG AAC TTT TCT GTG AAG GAC AGG TGT CTG TTT GCC    3264
Leu Glu Lys Gln Lys Asn Phe Ser Val Lys Asp Arg Cys Leu Phe Ala
        1075                1080                1085

TCC TTC CTA ACC ATT GCA CTG CAA ACC AAG CTG GTC TAC CTG ACC AGC    3312
Ser Phe Leu Thr Ile Ala Leu Gln Thr Lys Leu Val Tyr Leu Thr Ser
        1090                1095                1100

ATC CTA GAG GTG CTG ACC AGG GAC TTG ATG GAA CAG TGT AGT AAC ATG    3360
Ile Leu Glu Val Leu Thr Arg Asp Leu Met Glu Gln Cys Ser Asn Met
1105                1110                1115                1120
```

```
CAG CCG AAA CTC ATG CTG AGA CGC ACG GAG TCC GTC GTC GAA AAA CTC      3408
Gln Pro Lys Leu Met Leu Arg Arg Thr Glu Ser Val Val Glu Lys Leu
                1125                1130                1135

CTC ACA AAC TGG ATG TCC GTC TGC CTT TCT GGA TTT CTC CGG GAG ACT      3456
Leu Thr Asn Trp Met Ser Val Cys Leu Ser Gly Phe Leu Arg Glu Thr
                1140                1145                1150

GTC GGA GAG CCC TTC TAT TTG CTG GTG ACG ACT CTG AAC CAG AAA ATT      3504
Val Gly Glu Pro Phe Tyr Leu Leu Val Thr Thr Leu Asn Gln Lys Ile
                1155                1160                1165

AAC AAG GGT CCC GTG GAT GTA ATC ACT TGC AAA GCC CTG TAC ACA CTT      3552
Asn Lys Gly Pro Val Asp Val Ile Thr Cys Lys Ala Leu Tyr Thr Leu
1170                1175                1180

AAT GAA GAC TGG CTG TTG TGG CAG GTT CCG GAA TTC AGT ACT GTG GCA      3600
Asn Glu Asp Trp Leu Leu Trp Gln Val Pro Glu Phe Ser Thr Val Ala
1185                1190                1195                1200

TTA AAC GTC GTC TTT GAA AAA ATC CCG GAA AAC GAG AGT GCA GAT GTC      3648
Leu Asn Val Val Phe Glu Lys Ile Pro Glu Asn Glu Ser Ala Asp Val
                1205                1210                1215

TGT CGG AAT ATT TCA GTC AAT GTT CTC GAC TGT GAC ACC ATT GGC CAA      3696
Cys Arg Asn Ile Ser Val Asn Val Leu Asp Cys Asp Thr Ile Gly Gln
                1220                1225                1230

GCC AAA GAA AAG ATT TTC CAA GCA TTC TTA AGC AAA AAT GGC TCT CCT      3744
Ala Lys Glu Lys Ile Phe Gln Ala Phe Leu Ser Lys Asn Gly Ser Pro
                1235                1240                1245

TAT GGA CTT CAG CTT AAT GAA ATT GGT CTT GAG CTT CAA ATG GGC ACA      3792
Tyr Gly Leu Gln Leu Asn Glu Ile Gly Leu Glu Leu Gln Met Gly Thr
                1250                1255                1260

CGA CAG AAA GAA CTT CTG GAC ATC GAC AGT TCC TCC GTG ATT CTT GAA      3840
Arg Gln Lys Glu Leu Leu Asp Ile Asp Ser Ser Ser Val Ile Leu Glu
1265                1270                1275                1280

GAT GGA ATC ACC AAG CTA AAC ACC ATT GGC CAC TAT GAG ATA TCA AAT      3888
Asp Gly Ile Thr Lys Leu Asn Thr Ile Gly His Tyr Glu Ile Ser Asn
                1285                1290                1295

GGA TCC ACT ATA AAA GTC TTT AAG AAG ATA GCA AAT TTT ACT TCA GAT      3936
Gly Ser Thr Ile Lys Val Phe Lys Lys Ile Ala Asn Phe Thr Ser Asp
                1300                1305                1310

GTG GAG TAC TCG GAT GAC CAC TGC CAT TTG ATT TTA CCA GAT TCG GAA      3984
Val Glu Tyr Ser Asp Asp His Cys His Leu Ile Leu Pro Asp Ser Glu
                1315                1320                1325

GCA TTC CAA GAT GTG CAA GGA AAG AGA CAT CGA GGG AAG CAC AAG TTC      4032
Ala Phe Gln Asp Val Gln Gly Lys Arg His Arg Gly Lys His Lys Phe
                1330                1335                1340

AAA GTA AAA GAA ATG TAT CTG ACA AAG CTG CTG TCG ACC AAG GTG GCA      4080
Lys Val Lys Glu Met Tyr Leu Thr Lys Leu Leu Ser Thr Lys Val Ala
1345                1350                1355                1360

ATT CAT TCT GTG CTT GAA AAA CTT TTT AGA AGC ATT TGG AGT TTA CCC      4128
Ile His Ser Val Leu Glu Lys Leu Phe Arg Ser Ile Trp Ser Leu Pro
                1365                1370                1375

AAC AGC AGA GCT CCA TTT GCT ATA AAA TAC TTT TTT GAC TTT TTG GAC      4176
Asn Ser Arg Ala Pro Phe Ala Ile Lys Tyr Phe Phe Asp Phe Leu Asp
                1380                1385                1390

GCC CAG GCT GAA AAC AAA AAA ATC ACA GAT CCT GAC GTC GTA CAT ATT      4224
Ala Gln Ala Glu Asn Lys Lys Ile Thr Asp Pro Asp Val Val His Ile
                1395                1400                1405

TGG AAA ACA AAC AGC CTT CCT CTT CGC TTC TGG GTA AAC ATC CTG AAG      4272
Trp Lys Thr Asn Ser Leu Pro Leu Arg Phe Trp Val Asn Ile Leu Lys
1410                1415                1420

AAC CCT CAG TTT GTC TTT GAC ATT AAG AAG ACA CCA CAT ATA GAC GGC      4320
Asn Pro Gln Phe Val Phe Asp Ile Lys Lys Thr Pro His Ile Asp Gly
```

```
1425              1430              1435              1440

TGT TTG TCA GTG ATT GCC CAG GCA TTC ATG GAT GCA TTT TCT CTC ACA        4368
Cys Leu Ser Val Ile Ala Gln Ala Phe Met Asp Ala Phe Ser Leu Thr
                1445             1450             1455

GAG CAG CAA CTA GGG AAG GAA GCA CCA ACT AAT AAG CTT CTC TAT GCC        4416
Glu Gln Gln Leu Gly Lys Glu Ala Pro Thr Asn Lys Leu Leu Tyr Ala
            1460             1465             1470

AAG GAT ATC CCA ACC TAC AAA GAA GAA GTA AAA TCT TAT TAC AAA GCA        4464
Lys Asp Ile Pro Thr Tyr Lys Glu Glu Val Lys Ser Tyr Tyr Lys Ala
            1475             1480             1485

ATC AGG GAT TTG CCT CCA TTG TCA TCC TCA GAA ATG GAA GAA TTT TTA        4512
Ile Arg Asp Leu Pro Pro Leu Ser Ser Ser Glu Met Glu Glu Phe Leu
            1490             1495             1500

ACT CAG GAA TCT AAG AAA CAT GAA AAT GAA TTT AAT GAA GAA GTG GCC        4560
Thr Gln Glu Ser Lys Lys His Glu Asn Glu Phe Asn Glu Glu Val Ala
1505             1510             1515             1520

TTG ACA GAA ATT TAC AAA TAC ATC GTA AAA TAT TTT GAT GAG ATT CTA        4608
Leu Thr Glu Ile Tyr Lys Tyr Ile Val Lys Tyr Phe Asp Glu Ile Leu
                1525             1530             1535

AAT AAA CTA GAA AGA GAA CGA GGG CTG GAA GAA GCT CAG AAA CAA CTC        4656
Asn Lys Leu Glu Arg Glu Arg Gly Leu Glu Glu Ala Gln Lys Gln Leu
            1540             1545             1550

TTG CAT GTA AAA GTC TTA TTT GAT GAA AAG AAG AAA TGC AAG TGG ATG        4704
Leu His Val Lys Val Leu Phe Asp Glu Lys Lys Lys Cys Lys Trp Met
            1555             1560             1565

TAA                                                                    4707
*

(2) INFORMATION FOR SEQ ID NO:2:

(i) SEQUENCE CHARACTERISTICS:
        (A) LENGTH: 1568 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Val Ser Arg Arg Lys Ala Pro Pro Arg Pro Arg Pro Ala
 1               5              10              15

Ala Pro Leu Pro Leu Leu Ala Tyr Leu Leu Ala Leu Ala Pro Gly
            20              25              30

Arg Gly Ala Asp Glu Pro Val Trp Arg Ser Gln Ala Ile Gly Ala
        35              40              45

Ile Ala Ala Ser Gln Glu Asp Gly Val Phe Val Ala Ser Gly Ser Cys
    50              55              60

Leu Asp Gln Leu Asp Tyr Ser Leu Glu His Ser Leu Ser Arg Leu Tyr
65              70              75              80

Arg Asp Gln Ala Gly Asn Cys Thr Glu Pro Val Ser Leu Ala Pro Pro
                85              90              95

Ala Arg Pro Arg Pro Gly Ser Ser Phe Ser Lys Leu Leu Leu Pro Tyr
            100             105             110

Arg Glu Gly Ala Ala Gly Leu Gly Gly Leu Leu Leu Thr Gly Trp Thr
            115             120             125

Phe Asp Arg Gly Ala Cys Glu Val Arg Pro Leu Gly Asn Leu Ser Arg
    130             135             140

Asn Ser Leu Arg Asn Gly Thr Glu Val Val Ser Cys His Pro Gln Gly
145             150             155             160
```

-continued

```
Ser Thr Ala Gly Val Val Tyr Arg Ala Gly Arg Asn Asn Arg Trp Tyr
            165                 170                 175
Leu Ala Val Ala Ala Thr Tyr Val Leu Pro Glu Pro Glu Thr Ala Ser
            180                 185                 190
Arg Cys Asn Pro Ala Ala Ser Asp His Asp Thr Ala Ile Ala Leu Lys
            195                 200                 205
Asp Thr Glu Gly Arg Ser Leu Ala Thr Gln Leu Gly Arg Leu Lys
            210                 215                 220
Leu Cys Glu Gly Ala Gly Ser Leu His Phe Val Asp Ala Phe Leu Trp
225                 230                 235                 240
Asn Gly Ser Ile Tyr Phe Pro Tyr Tyr Pro Tyr Asn Tyr Thr Ser Gly
            245                 250                 255
Ala Ala Thr Gly Trp Pro Ser Met Ala Arg Ile Ala Gln Ser Thr Glu
            260                 265                 270
Val Leu Phe Gln Gly Gln Ala Ser Leu Asp Cys Gly His Gly His Pro
            275                 280                 285
Asp Gly Arg Arg Leu Leu Leu Ser Ser Ser Leu Val Glu Ala Leu Asp
            290                 295                 300
Val Trp Ala Gly Val Phe Ser Ala Ala Gly Glu Gly Gln Glu Arg
305                 310                 315                 320
Arg Ser Pro Thr Thr Thr Ala Leu Cys Leu Phe Arg Met Ser Glu Ile
            325                 330                 335
Gln Ala Arg Ala Lys Arg Val Ser Trp Asp Phe Lys Thr Ala Glu Ser
            340                 345                 350
His Cys Lys Glu Gly Asp Gln Pro Glu Arg Val Gln Pro Ile Ala Ser
            355                 360                 365
Ser Thr Leu Ile His Ser Asp Leu Thr Ser Val Tyr Gly Thr Val Val
            370                 375                 380
Met Asn Arg Thr Val Leu Phe Leu Gly Thr Gly Asp Gly Gln Leu Leu
385                 390                 395                 400
Lys Val Ile Leu Gly Glu Asn Leu Thr Ser Asn Cys Pro Glu Val Ile
            405                 410                 415
Tyr Glu Ile Lys Glu Glu Thr Pro Val Phe Tyr Lys Leu Val Pro Asp
            420                 425                 430
Pro Val Lys Asn Ile Tyr Ile Tyr Leu Thr Ala Gly Lys Glu Val Arg
            435                 440                 445
Arg Ile Arg Val Ala Asn Cys Asn Lys His Lys Ser Cys Ser Glu Cys
450                 455                 460
Leu Thr Ala Thr Asp Pro His Cys Gly Trp Cys His Ser Leu Gln Arg
465                 470                 475                 480
Cys Thr Phe Gln Gly Asp Cys Val His Ser Glu Asn Leu Glu Asn Trp
            485                 490                 495
Leu Asp Ile Ser Ser Gly Ala Lys Lys Cys Pro Lys Ile Gln Ile Ile
            500                 505                 510
Arg Ser Ser Lys Glu Lys Thr Thr Val Thr Met Val Gly Ser Phe Ser
            515                 520                 525
Pro Arg His Ser Lys Cys Met Val Lys Asn Val Asp Ser Ser Arg Glu
            530                 535                 540
Leu Cys Gln Asn Lys Ser Gln Pro Asn Arg Thr Cys Thr Cys Ser Ile
545                 550                 555                 560
Pro Thr Arg Ala Thr Tyr Lys Asp Val Ser Val Asn Val Met Phe
            565                 570                 575
Ser Phe Gly Ser Trp Asn Leu Ser Asp Arg Phe Asn Phe Thr Asn Cys
```

-continued

```
                580                 585                 590
Ser Ser Leu Lys Glu Cys Pro Ala Cys Val Glu Thr Gly Cys Ala Trp
            595                 600                 605
Cys Lys Ser Ala Arg Arg Cys Ile His Pro Phe Thr Ala Cys Asp Pro
610                 615                 620
Ser Asp Tyr Glu Arg Asn Gln Glu Gln Cys Pro Val Ala Val Glu Lys
625                 630                 635                 640
Thr Ser Gly Gly Arg Pro Lys Glu Asn Lys Gly Asn Arg Thr Asn
                645                 650                 655
Gln Ala Leu Gln Val Phe Tyr Ile Lys Ser Ile Glu Pro Gln Lys Val
            660                 665                 670
Ser Thr Leu Gly Lys Ser Asn Val Ile Val Thr Gly Ala Asn Phe Thr
            675                 680                 685
Arg Ala Ser Asn Ile Thr Met Ile Leu Lys Gly Thr Ser Thr Cys Asp
690                 695                 700
Lys Asp Val Ile Gln Val Ser His Val Leu Asn Asp Thr His Met Lys
705                 710                 715                 720
Phe Ser Leu Pro Ser Ser Arg Lys Glu Met Lys Asp Val Cys Ile Gln
                725                 730                 735
Phe Asp Gly Gly Asn Cys Ser Ser Val Gly Ser Leu Ser Tyr Ile Ala
                740                 745                 750
Leu Pro His Cys Ser Leu Ile Phe Pro Ala Thr Thr Trp Ile Ser Gly
            755                 760                 765
Gly Gln Asn Ile Thr Met Met Gly Arg Asn Phe Asp Val Ile Asp Asn
770                 775                 780
Leu Ile Ile Ser His Glu Leu Lys Gly Asn Ile Asn Val Ser Glu Tyr
785                 790                 795                 800
Cys Val Ala Thr Tyr Cys Gly Phe Leu Ala Pro Ser Leu Lys Ser Ser
                805                 810                 815
Lys Val Arg Thr Asn Val Thr Val Lys Leu Arg Val Gln Asp Thr Tyr
                820                 825                 830
Leu Asp Cys Gly Thr Leu Gln Tyr Arg Glu Asp Pro Arg Phe Thr Gly
            835                 840                 845
Tyr Arg Val Glu Ser Glu Val Asp Thr Glu Leu Glu Val Lys Ile Gln
850                 855                 860
Lys Glu Asn Asp Asn Phe Asn Ile Ser Lys Lys Asp Ile Glu Ile Thr
865                 870                 875                 880
Leu Phe His Gly Glu Asn Gly Gln Leu Asn Cys Ser Phe Glu Asn Ile
                885                 890                 895
Thr Arg Asn Gln Asp Leu Thr Thr Ile Leu Cys Lys Ile Lys Gly Ile
                900                 905                 910
Lys Thr Ala Ser Thr Ile Ala Asn Ser Ser Lys Lys Val Arg Val Lys
            915                 920                 925
Leu Gly Asn Leu Glu Leu Tyr Val Glu Gln Glu Ser Val Pro Ser Thr
930                 935                 940
Trp Tyr Phe Leu Ile Val Leu Pro Val Leu Leu Val Ile Val Ile Phe
945                 950                 955                 960
Ala Ala Val Gly Val Thr Arg His Lys Ser Lys Glu Leu Ser Arg Lys
                965                 970                 975
Gln Ser Gln Gln Leu Glu Leu Leu Glu Ser Glu Leu Arg Lys Glu Ile
            980                 985                 990
Arg Asp Gly Phe Ala Glu Leu Gln Met Asp Lys Leu Asp Val Val Asp
            995                 1000                1005
```

-continued

```
Ser Phe Gly Thr Val Pro Phe Leu Asp Tyr Lys His Phe Ala Leu Arg
    1010                1015                1020

Thr Phe Phe Pro Glu Ser Gly Gly Phe Thr His Ile Phe Thr Glu Asp
1025                1030                1035                1040

Met His Asn Arg Asp Ala Asn Asp Lys Asn Glu Ser Leu Thr Ala Leu
                1045                1050                1055

Asp Ala Leu Ile Cys Asn Lys Ser Phe Leu Val Thr Val Ile His Thr
                1060                1065                1070

Leu Glu Lys Gln Lys Asn Phe Ser Val Lys Asp Arg Cys Leu Phe Ala
            1075                1080                1085

Ser Phe Leu Thr Ile Ala Leu Gln Thr Lys Leu Val Tyr Leu Thr Ser
    1090                1095                1100

Ile Leu Glu Val Leu Thr Arg Asp Leu Met Glu Gln Cys Ser Asn Met
1105                1110                1115                1120

Gln Pro Lys Leu Met Leu Arg Arg Thr Glu Ser Val Val Glu Lys Leu
                1125                1130                1135

Leu Thr Asn Trp Met Ser Val Cys Leu Ser Gly Phe Leu Arg Glu Thr
                1140                1145                1150

Val Gly Glu Pro Phe Tyr Leu Leu Val Thr Thr Leu Asn Gln Lys Ile
            1155                1160                1165

Asn Lys Gly Pro Val Asp Val Ile Thr Cys Lys Ala Leu Tyr Thr Leu
    1170                1175                1180

Asn Glu Asp Trp Leu Leu Trp Gln Val Pro Glu Phe Ser Thr Val Ala
1185                1190                1195                1200

Leu Asn Val Val Phe Glu Lys Ile Pro Glu Asn Glu Ser Ala Asp Val
                1205                1210                1215

Cys Arg Asn Ile Ser Val Asn Val Leu Asp Cys Asp Thr Ile Gly Gln
                1220                1225                1230

Ala Lys Glu Lys Ile Phe Gln Ala Phe Leu Ser Lys Asn Gly Ser Pro
            1235                1240                1245

Tyr Gly Leu Gln Leu Asn Glu Ile Gly Leu Glu Leu Gln Met Gly Thr
    1250                1255                1260

Arg Gln Lys Glu Leu Leu Asp Ile Asp Ser Ser Ser Val Ile Leu Glu
1265                1270                1275                1280

Asp Gly Ile Thr Lys Leu Asn Thr Ile Gly His Tyr Glu Ile Ser Asn
                1285                1290                1295

Gly Ser Thr Ile Lys Val Phe Lys Ile Ala Asn Phe Thr Ser Asp
            1300                1305                1310

Val Glu Tyr Ser Asp Asp His Cys His Leu Ile Leu Pro Asp Ser Glu
    1315                1320                1325

Ala Phe Gln Asp Val Gln Gly Lys Arg His Arg Gly Lys His Lys Phe
    1330                1335                1340

Lys Val Lys Glu Met Tyr Leu Thr Lys Leu Leu Ser Thr Lys Val Ala
1345                1350                1355                1360

Ile His Ser Val Leu Glu Lys Leu Phe Arg Ser Ile Trp Ser Leu Pro
                1365                1370                1375

Asn Ser Arg Ala Pro Phe Ala Ile Lys Tyr Phe Phe Asp Phe Leu Asp
            1380                1385                1390

Ala Gln Ala Glu Asn Lys Lys Ile Thr Asp Pro Asp Val His Ile
            1395                1400                1405

Trp Lys Thr Asn Ser Leu Pro Leu Arg Phe Trp Val Asn Ile Leu Lys
1410                1415                1420
```

```
Asn Pro Gln Phe Val Phe Asp Ile Lys Lys Thr Pro His Ile Asp Gly
1425                1430                1435                1440

Cys Leu Ser Val Ile Ala Gln Ala Phe Met Asp Ala Phe Ser Leu Thr
                1445                1450                1455

Glu Gln Gln Leu Gly Lys Glu Ala Pro Thr Asn Lys Leu Leu Tyr Ala
                1460                1465                1470

Lys Asp Ile Pro Thr Tyr Lys Glu Glu Val Lys Ser Tyr Tyr Lys Ala
            1475                1480                1485

Ile Arg Asp Leu Pro Pro Leu Ser Ser Ser Glu Met Glu Glu Phe Leu
            1490                1495                1500

Thr Gln Glu Ser Lys Lys His Glu Asn Glu Phe Asn Glu Glu Val Ala
1505                1510                1515                1520

Leu Thr Glu Ile Tyr Lys Tyr Ile Val Lys Tyr Phe Asp Glu Ile Leu
                1525                1530                1535

Asn Lys Leu Glu Arg Glu Arg Gly Leu Glu Glu Ala Gln Lys Gln Leu
                1540                1545                1550

Leu His Val Lys Val Leu Phe Asp Glu Lys Lys Cys Lys Trp Met
        1555                1560                1565

*

(2) INFORMATION FOR SEQ ID NO:3:

(i) SEQUENCE CHARACTERISTICS:
        (A) LENGTH: 30 amino acids
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

TGTCACTAGT ATCGAATGGC ATAAGTTTGA A                               31

(2) INFORMATION FOR SEQ ID NO:4:

(i) SEQUENCE CHARACTERISTICS:
        (A) LENGTH: 32 amino acids
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:4:

GACAGCGGCC GCCTATTACA TTTTAAGTAT TTT                             33

(2) INFORMATION FOR SEQ ID NO:5:

(i) SEQUENCE CHARACTERISTICS:
        (A) LENGTH: 17 amino acids
        (B) TYPE: nucleic acid
        (C) STRANDEDNESS: single
        (D) TOPOLOGY: linear (ii) MOLECULE TYPE: primer (iii) HYPOTHETICAL: NO (iv) ANTI-SENSE: NO (ix) FEATURE:
```

```
          (A) NAME/KEY:
          (B) LOCATION:

(xi) SEQUENCE DESCRIPTION: SEQ ID NO:5:

GCGGGACTCA GAGTCACC                                                    18

(2) INFORMATION FOR SEQ ID NO:6:

(i) SEQUENCE CHARACTERISTICS:
          (A) LENGTH:  42 amino acids
          (B) TYPE: nucleic acid
          (C) STRANDEDNESS: single
          (D) TOPOLOGY: linear (ii) MOLECULE TYPE: primer (iii) HYPOTHETICAL: NO (iv) ANTI-SENSE: NO (xi) SEQUENCE DESCRIPTION: SEQ ID NO:6:

GGATCCTAAT ACGACTCACT ATAGGGAGGA AACCACTCCG AAC                        43

(2) INFORMATION FOR SEQ ID NO:7:

(i) SEQUENCE CHARACTERISTICS:
          (A) LENGTH:  1982 amino acids
          (B) TYPE: nucleic acid
          (C) STRANDEDNESS: single
          (D) TOPOLOGY: linear (ii) MOLECULE TYPE: cDNA (iii) HYPOTHETICAL: NO (iv) ANTI-SENSE: NO (ix) FEATURE:
          (A) NAME/KEY: CDS
          (B) LOCATION: 1..1983

(xi) SEQUENCE DESCRIPTION: SEQ ID NO:7:

ATG TTC CAT GTT TCT TTT AGA TAT ATC TTT GGA ATT CCT CCA CTG ATC        48
Met Phe His Val Ser Phe Arg Tyr Ile Phe Gly Ile Pro Pro Leu Ile
 1               5                  10                  15

CTT GTT CTG CTG CCT GTC ACT AGC TCT GAC TAC AAA GAT GAC GAT GAT        96
Leu Val Leu Leu Pro Val Thr Ser Ser Asp Tyr Lys Asp Asp Asp Asp
                20                  25                  30

AAA AGA TCT TGT GAC AAA ACT CAC ACA TGC CCA CCG TGC CCA GCA CCT       144
Lys Arg Ser Cys Asp Lys Thr His Thr Cys Pro Pro Cys Pro Ala Pro
            35                  40                  45

GAA GCC GAG GGC GCG CCG TCA GTC TTC CTC TTC CCC CCA AAA CCC AAG       192
Glu Ala Glu Gly Ala Pro Ser Val Phe Leu Phe Pro Pro Lys Pro Lys
 50                  55                  60

GAC ACC CTC ATG ATC TCC CGG ACC CCT GAG GTC ACA TGC GTG GTG GTG       240
Asp Thr Leu Met Ile Ser Arg Thr Pro Glu Val Thr Cys Val Val Val
 65                  70                  75                  80

GAC GTG AGC CAC GAA GAC CCT GAG GTC AAG TTC AAC TGG TAC GTG GAC       288
Asp Val Ser His Glu Asp Pro Glu Val Lys Phe Asn Trp Tyr Val Asp
                85                  90                  95

GGC GTG GAG GTG CAT AAT GCC AAG ACA AAG CCG CGG GAG GAG CAG TAC       336
Gly Val Glu Val His Asn Ala Lys Thr Lys Pro Arg Glu Glu Gln Tyr
                100                 105                 110

AAC AGC ACG TAC CGT GTG GTC AGC GTC CTC ACC GTC CTG CAC CAG GAC       384
Asn Ser Thr Tyr Arg Val Val Ser Val Leu Thr Val Leu His Gln Asp
            115                 120                 125
```

| | | |
|---|---|---|
| TGG CTG AAT GGC AAG GAG TAC AAG TGC AAG GTC TCC AAC AAA GCC CTC<br>Trp Leu Asn Gly Lys Glu Tyr Lys Cys Lys Val Ser Asn Lys Ala Leu<br>130                                   135                             140 | 432 |
| CCA GCC CCC ATC GAG AAA ACC ATC TCC AAA GCC AAA GGG CAG CCC CGA<br>Pro Ala Pro Ile Glu Lys Thr Ile Ser Lys Ala Lys Gly Gln Pro Arg<br>145                               150                          155                       160 | 480 |
| GAA CCA CAG GTG TAC ACC CTG CCC CCA TCC CGG GAG GAG ATG ACC AAG<br>Glu Pro Gln Val Tyr Thr Leu Pro Pro Ser Arg Glu Glu Met Thr Lys<br>                     165                          170                          175 | 528 |
| AAC CAG GTC AGC CTG ACC TGC CTG GTC AAA GGC TTC TAT CCC AGC GAC<br>Asn Gln Val Ser Leu Thr Cys Leu Val Lys Gly Phe Tyr Pro Ser Asp<br>                180                          185                          190 | 576 |
| ATC GCC GTG GAG TGG GAG AGC AAT GGG CAG CCG GAG AAC AAC TAC AAG<br>Ile Ala Val Glu Trp Glu Ser Asn Gly Gln Pro Glu Asn Asn Tyr Lys<br>               195                          200                         205 | 624 |
| ACC ACG CCT CCC GTG CTG GAC TCC GAC GGC TCC TTC TTC CTC TAT AGC<br>Thr Thr Pro Pro Val Leu Asp Ser Asp Gly Ser Phe Phe Leu Tyr Ser<br>210                                   215                          220 | 672 |
| AAG CTC ACC GTG GAC AAG AGC AGG TGG CAG CAG GGG AAC GTC TTC TCA<br>Lys Leu Thr Val Asp Lys Ser Arg Trp Gln Gln Gly Asn Val Phe Ser<br>225                                   230                          235                       240 | 720 |
| TGC TCC GTG ATG CAT GAG GCT CTG CAC AAC CAC TAC ACG CAG AAG AGC<br>Cys Ser Val Met His Glu Ala Leu His Asn His Tyr Thr Gln Lys Ser<br>                245                          250                          255 | 768 |
| CTC TCC CTG TCT CCG GGT AAA GGA GGG GGC GGA TCA GGG GGC GGA GGA<br>Leu Ser Leu Ser Pro Gly Lys Gly Gly Gly Gly Ser Gly Gly Gly Gly<br>                     260                          265                          270 | 816 |
| TCT ACT AGT ATC GAA TGG CAT AAG TTT GAA ACG AGT GAA GAA ATA ATT<br>Ser Thr Ser Ile Glu Trp His Lys Phe Glu Thr Ser Glu Glu Ile Ile<br>                275                          280                          285 | 864 |
| TCT ACT TAC TTA ATA GAT GAT GTA TTA TAC ACG GGC GTT AAT GGG GCG<br>Ser Thr Tyr Leu Ile Asp Asp Val Leu Tyr Thr Gly Val Asn Gly Ala<br>290                                   295                          300 | 912 |
| GTA TAT ACA TTT TCA AAT AAT GAA CTA AAC AAA ACT GGT TTA ACT AAT<br>Val Tyr Thr Phe Ser Asn Asn Glu Leu Asn Lys Thr Gly Leu Thr Asn<br>305                                   310                          315                       320 | 960 |
| AAC AAT AAT TAT ATC ACA ACA TCT ATA AAA GTA GAG GAT ACA TTA GTA<br>Asn Asn Asn Tyr Ile Thr Thr Ser Ile Lys Val Glu Asp Thr Leu Val<br>                325                          330                          335 | 1008 |
| TGC GGA ACC AAT AAC GGA AAC CCC AAA TGT TGG AAA ATA GAC GGT TCC<br>Cys Gly Thr Asn Asn Gly Asn Pro Lys Cys Trp Lys Ile Asp Gly Ser<br>                     340                          345                          350 | 1056 |
| GAA GAT CCA AAA TAT AGA GGT AGA GGA TAT GCT CCT TAT CAA AAT AGT<br>Glu Asp Pro Lys Tyr Arg Gly Arg Gly Tyr Ala Pro Tyr Gln Asn Ser<br>                     355                          360                          365 | 1104 |
| AAA GTG ACG ATA ATC AGT CAT AAC GAA TGT GTA CTA TCT GAT ATA AAC<br>Lys Val Thr Ile Ile Ser His Asn Glu Cys Val Leu Ser Asp Ile Asn<br>370                                   375                          380 | 1152 |
| ATA TCA AAA GAA GGA ATT AAA AGA TGG AGA AGA TTT GAC GGA CCA TGT<br>Ile Ser Lys Glu Gly Ile Lys Arg Trp Arg Arg Phe Asp Gly Pro Cys<br>385                                   390                          395                       400 | 1200 |
| GGT TAT GAT TTA TAC ACG GCA GAT AAC GTG ATT CCA AAA GAT GGT GTG<br>Gly Tyr Asp Leu Tyr Thr Ala Asp Asn Val Ile Pro Lys Asp Gly Val<br>                                 405                          410                          415 | 1248 |
| CGT GGA GCA TTC GTT GAT AAA GAC GGC ACT TAT GAC AAA GTT TAC ATT<br>Arg Gly Ala Phe Val Asp Lys Asp Gly Thr Tyr Asp Lys Val Tyr Ile<br>                         420                          425                          430 | 1296 |
| CTT TTC ACT GAT ACT ATC GAC ACA AAG AGA ATT GTT AAA ATT CCG TAT<br>Leu Phe Thr Asp Thr Ile Asp Thr Lys Arg Ile Val Lys Ile Pro Tyr<br>435                                 440                          445 | 1344 |

```
ATA GCA CAA ATG TGC TTA AAT GAC GAA GGT GGT CCA TCA TCA TTG TCT    1392
Ile Ala Gln Met Cys Leu Asn Asp Glu Gly Gly Pro Ser Ser Leu Ser
        450                 455                 460

AGT CAT AGA TGG TCG ACG TTT CTC AAG GTC GAA TTA GAA TGT GAT ATC    1440
Ser His Arg Trp Ser Thr Phe Leu Lys Val Glu Leu Glu Cys Asp Ile
465                 470                 475                 480

GAC GGA AGA AGT TAT AGA CAA ATT ATT CAT TCT AAA GCT ATA AAA ACA    1488
Asp Gly Arg Ser Tyr Arg Gln Ile Ile His Ser Lys Ala Ile Lys Thr
                485                 490                 495

GAT AAT GAT ACG ATA CTA TAT GTA TTC TTT GAT AGT CCT TAT TCC AAG    1536
Asp Asn Asp Thr Ile Leu Tyr Val Phe Phe Asp Ser Pro Tyr Ser Lys
            500                 505                 510

TCC GCA TTA TGT ACC TAT TCT ATG AAT GCC ATT AAA CAC TCT TTT TCT    1584
Ser Ala Leu Cys Thr Tyr Ser Met Asn Ala Ile Lys His Ser Phe Ser
        515                 520                 525

ACG TCA AAA TTG GGA GGA TAT ACA AAG CAA TTG CCG TCT CCA GCT CCT    1632
Thr Ser Lys Leu Gly Gly Tyr Thr Lys Gln Leu Pro Ser Pro Ala Pro
    530                 535                 540

GGT ATA TGT CTA CCA GCT GGA AAA GTT GTT CCA CAT ACC ACG TTT GAC    1680
Gly Ile Cys Leu Pro Ala Gly Lys Val Val Pro His Thr Thr Phe Asp
545                 550                 555                 560

ATC ATA GAA CAA TAT AAT GAG CTA GAT GAT ATT ATA AAG CCT TTA TCT    1728
Ile Ile Glu Gln Tyr Asn Glu Leu Asp Asp Ile Ile Lys Pro Leu Ser
                565                 570                 575

CAA CCT ATC TTC GAA GGA CCG TCT GGT GTT AAA TGG TTC GAT ATA AAG    1776
Gln Pro Ile Phe Glu Gly Pro Ser Gly Val Lys Trp Phe Asp Ile Lys
            580                 585                 590

GAG AAG GAA AAT GAA CAT CGG GAA TAT AGA ATA TAC TTC ATA AAA GAA    1824
Glu Lys Glu Asn Glu His Arg Glu Tyr Arg Ile Tyr Phe Ile Lys Glu
        595                 600                 605

AAT ACT ATA TAT TCG TTC GAT ACA AAA TCT AAA CAA ACT CGT AGT GCA    1872
Asn Thr Ile Tyr Ser Phe Asp Thr Lys Ser Lys Gln Thr Arg Ser Ala
    610                 615                 620

CAA GTT GAT GCG CGA CTA TTT TCA GTA ATG GTA ACT TCG AAA CCG TTA    1920
Gln Val Asp Ala Arg Leu Phe Ser Val Met Val Thr Ser Lys Pro Leu
625                 630                 635                 640

TTT ATA GCA GAT ATA GGG ATA GGA GTA GGA ATA CCA CGA ATG AAA AAA    1968
Phe Ile Ala Asp Ile Gly Ile Gly Val Gly Ile Pro Arg Met Lys Lys
                645                 650                 655

ATA CTT AAA ATG TAA                                                1983
Ile Leu Lys Met
        660

(2) INFORMATION FOR SEQ ID NO:8:

(i) SEQUENCE CHARACTERISTICS:
        (A) LENGTH:  660 amino acids
        (B) TYPE: amino acid
        (D) TOPOLOGY: linear (ii) MOLECULE TYPE: protein (xi) SEQUENCE DESCRIPTION: SEQ ID NO:8:

Met Phe His Val Ser Phe Arg Tyr Ile Phe Gly Ile Pro Pro Leu Ile
1               5                   10                  15

Leu Val Leu Leu Pro Val Thr Ser Ser Asp Tyr Lys Asp Asp Asp
            20                  25                  30

Lys Arg Ser Cys Asp Lys Thr His Thr Cys Pro Pro Cys Pro Ala Pro
        35                  40                  45

Glu Ala Glu Gly Ala Pro Ser Val Phe Leu Phe Pro Pro Lys Pro Lys
```

-continued

```
            50                  55                  60
Asp Thr Leu Met Ile Ser Arg Thr Pro Glu Val Thr Cys Val Val Val
 65                  70                  75                  80

Asp Val Ser His Glu Asp Pro Glu Val Lys Phe Asn Trp Tyr Val Asp
                 85                  90                  95

Gly Val Glu Val His Asn Ala Lys Thr Lys Pro Arg Glu Glu Gln Tyr
                100                 105                 110

Asn Ser Thr Tyr Arg Val Val Ser Val Leu Thr Val Leu His Gln Asp
                115                 120                 125

Trp Leu Asn Gly Lys Glu Tyr Lys Cys Lys Val Ser Asn Lys Ala Leu
130                 135                 140

Pro Ala Pro Ile Glu Lys Thr Ile Ser Lys Ala Lys Gly Gln Pro Arg
145                 150                 155                 160

Glu Pro Gln Val Tyr Thr Leu Pro Pro Ser Arg Glu Glu Met Thr Lys
                165                 170                 175

Asn Gln Val Ser Leu Thr Cys Leu Val Lys Gly Phe Tyr Pro Ser Asp
                180                 185                 190

Ile Ala Val Glu Trp Glu Ser Asn Gly Gln Pro Glu Asn Asn Tyr Lys
                195                 200                 205

Thr Thr Pro Pro Val Leu Asp Ser Asp Gly Ser Phe Phe Leu Tyr Ser
210                 215                 220

Lys Leu Thr Val Asp Lys Ser Arg Trp Gln Gln Gly Asn Val Phe Ser
225                 230                 235                 240

Cys Ser Val Met His Glu Ala Leu His Asn His Tyr Thr Gln Lys Ser
                245                 250                 255

Leu Ser Leu Ser Pro Gly Lys Gly Gly Gly Gly Ser Gly Gly Gly Gly
                260                 265                 270

Ser Thr Ser Ile Glu Trp His Lys Phe Glu Thr Ser Glu Glu Ile Ile
                275                 280                 285

Ser Thr Tyr Leu Ile Asp Asp Val Leu Tyr Thr Gly Val Asn Gly Ala
                290                 295                 300

Val Tyr Thr Phe Ser Asn Asn Glu Leu Asn Lys Thr Gly Leu Thr Asn
305                 310                 315                 320

Asn Asn Asn Tyr Ile Thr Thr Ser Ile Lys Val Glu Asp Thr Leu Val
                325                 330                 335

Cys Gly Thr Asn Asn Gly Asn Pro Lys Cys Trp Lys Ile Asp Gly Ser
                340                 345                 350

Glu Asp Pro Lys Tyr Arg Gly Arg Gly Tyr Ala Pro Tyr Gln Asn Ser
                355                 360                 365

Lys Val Thr Ile Ile Ser His Asn Glu Cys Val Leu Ser Asp Ile Asn
370                 375                 380

Ile Ser Lys Glu Gly Ile Lys Arg Trp Arg Arg Phe Asp Gly Pro Cys
385                 390                 395                 400

Gly Tyr Asp Leu Tyr Thr Ala Asp Asn Val Ile Pro Lys Asp Gly Val
                405                 410                 415

Arg Gly Ala Phe Val Asp Lys Asp Gly Thr Tyr Asp Lys Val Tyr Ile
                420                 425                 430

Leu Phe Thr Asp Thr Ile Asp Thr Lys Arg Ile Val Lys Ile Pro Tyr
                435                 440                 445

Ile Ala Gln Met Cys Leu Asn Asp Glu Gly Gly Pro Ser Ser Leu Ser
                450                 455                 460

Ser His Arg Trp Ser Thr Phe Leu Lys Val Glu Leu Glu Cys Asp Ile
465                 470                 475                 480
```

```
Asp Gly Arg Ser Tyr Arg Gln Ile Ile His Ser Lys Ala Ile Lys Thr
            485                 490                 495
Asp Asn Asp Thr Ile Leu Tyr Val Phe Phe Asp Ser Pro Tyr Ser Lys
            500                 505                 510
Ser Ala Leu Cys Thr Tyr Ser Met Asn Ala Ile Lys His Ser Phe Ser
            515                 520                 525
Thr Ser Lys Leu Gly Gly Tyr Thr Lys Gln Leu Pro Ser Pro Ala Pro
            530                 535                 540
Gly Ile Cys Leu Pro Ala Gly Lys Val Val Pro His Thr Thr Phe Asp
545                 550                 555                 560
Ile Ile Glu Gln Tyr Asn Glu Leu Asp Asp Ile Ile Lys Pro Leu Ser
                565                 570                 575
Gln Pro Ile Phe Glu Gly Pro Ser Gly Val Lys Trp Phe Asp Ile Lys
            580                 585                 590
Glu Lys Glu Asn Glu His Arg Glu Tyr Arg Ile Tyr Phe Ile Lys Glu
            595                 600                 605
Asn Thr Ile Tyr Ser Phe Asp Thr Lys Ser Lys Gln Thr Arg Ser Ala
            610                 615                 620
Gln Val Asp Ala Arg Leu Phe Ser Val Met Val Thr Ser Lys Pro Leu
625                 630                 635                 640
Phe Ile Ala Asp Ile Gly Ile Gly Val Gly Ile Pro Arg Met Lys Lys
                645                 650                 655
Ile Leu Lys Met
            660

(2) INFORMATION FOR SEQ ID NO:9:

(i) SEQUENCE CHARACTERISTICS:
        (A) LENGTH: 32 amino acids
        (B) TYPE: nucleic acid
        (C) STRANDEDNESS: single
        (D) TOPOLOGY: linear (ii) MOLECULE TYPE: primer (iii) HYPOTHETICAL: NO (iv) ANTI-SENSE: NO (xi) SEQUENCE DESCRIPTION: SEQ ID NO:9:

ATCGCATCAT CTACCTTCAT CCATTCCGAC CTG                              33

(2) INFORMATION FOR SEQ ID NO:10:

(i) SEQUENCE CHARACTERISTICS:
        (A) LENGTH: 32 amino acids
        (B) TYPE: nucleic acid
        (C) STRANDEDNESS: single
        (D) TOPOLOGY: linear (ii) MOLECULE TYPE: primer (iii) HYPOTHETICAL: NO (iv) ANTI-SENSE: NO (xi) SEQUENCE DESCRIPTION: SEQ ID NO:10:

TAAACACTCC GAACAGGATT TATGTTTATT GCA                              33
```